United States Patent [19]
Greenlee et al.

[11] Patent Number: 5,223,499
[45] Date of Patent: Jun. 29, 1993

[54] 6-AMINO SUBSTITUTED IMIDAZO[4,5-BIPYRIDINES AS ANGIOTENSIN II ANTAGONISTS

[75] Inventors: William J. Greenlee, Teaneck; Dooseop Kim, Scotch Plains; Nathan B. Mantlo, Westfield; Arthur A. Pastchett, Westfield; Ralph A. Rivero, Tinton Falls, all of N.J.

[73] Assignee: Merck & Co., Inc., Rahway, N.J.

[21] Appl. No.: 881,453

[22] Filed: May 11, 1992

Related U.S. Application Data

[63] Continuation-in-part of Ser. No. 516,286, May 4, 1990, which is a continuation-in-part of Ser. No. 358,971, May 30, 1989, abandoned.

[51] Int. Cl.$^5$ .............. C07D 471/04; A61K 31/535; A61K 31/435
[52] U.S. Cl. ..................... 514/234.5; 514/300; 544/127; 546/118
[58] Field of Search ....................... 546/118; 544/127; 514/300, 234.5

[56] References Cited

U.S. PATENT DOCUMENTS

| | | | |
|---|---|---|---|
| 4,722,929 | 2/1988 | Austel et al. | 546/118 |
| 5,049,565 | 9/1991 | Chen et al. | 546/118 |
| 5,053,329 | 10/1991 | Chen et al. | 546/118 |
| 5,057,522 | 10/1991 | Chen et al. | 546/118 |
| 5,066,586 | 11/1991 | Chen et al. | 546/118 |
| 5,087,702 | 2/1992 | Chen et al. | 546/118 |

FOREIGN PATENT DOCUMENTS

| | | |
|---|---|---|
| 400974 | 12/1990 | European Pat. Off. |
| 415886 | 3/1991 | European Pat. Off. |
| 420237 | 4/1991 | European Pat. Off. |
| 426021 | 5/1991 | European Pat. Off. |
| 434038 | 6/1991 | European Pat. Off. |
| 459136 | 12/1991 | European Pat. Off. |
| 461040 | 12/1991 | European Pat. Off. |
| 470543 | 2/1992 | European Pat. Off. |

OTHER PUBLICATIONS

Chang et al., Two Angiotensin II Binding Sites In Rat Brain Revealed Using [$^{125}$I]SAR$^1$,ILE$^8$-Angiotensin II And Selective Nonpeptide Antagonists, Biochem. and Biophy. Res. Comm., 171, pp. 813–817 (1990).
Stromberg, C. et al. Neuro. Report, 3; pp. 703–704 (1992).
Schiavone, M., et al., Hypertension, 17, No. 3, p. 425 (1991).
Gyurko, R. et al., Biochem. & Biophys. Research Communications, 186, No. 1 pp. 285–292 (1992).
Bottari, S. et al., Biochem. & Biophys. Research Communications, 183, No. 1 pp. 206–211 (1992).
Pratt, R. et al., Hypertension, 20, No. 3, p. 432 (1992).

*Primary Examiner*—Bernard Dentz
*Attorney, Agent, or Firm*—Joseph F. DiPrima; William H. Nicholson; Valerie J. Camara

[57] ABSTRACT

Substituted imidazo[4,5-b]pyridines of structural formula:

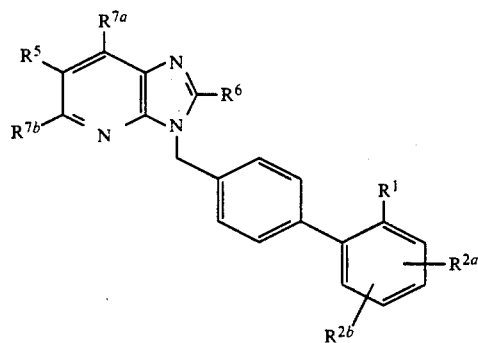

are angiotensin II antagonists useful in the treatment of hypertension and congestive heart failure.

18 Claims, No Drawings

6-AMINO SUBSTITUTED IMIDAZO[4,5-BIPYRIDINES AS ANGIOTENSIN II ANTAGONISTS

This is a continuation-in-part of copending application Ser. No. 516,286 filed May 4, 1990 which is a continuation-in-part application of copending application Ser. No. 358,971 filed May 30, 1989, now abandoned.

SUMMARY OF THE INVENTION

This invention relates to novel compounds of structural formula I which are angiotensin II (AII) antagonists that inhibit the binding of AII to the $AT_1$ and $AT_2$ receptor sites, useful in the treatment of hypertension, congestive heart failure, and elevated intraocular pressure.

It also relates to processes for preparing the novel compounds; pharmaceutical formulations comprising one or more of the compounds as active ingredient; and, a method of treatment of hypertension, congestive heart failure, and elevated intraocular pressure.

BACKGROUND OF THE INVENTION

Renin-angiotensin system (RAS) plays a central role in the regulation of normal blood pressure and seems to be critically involved in hypertension development and maintenance as well as congestive heart failure. Angiotensin II (AII), an octapeptide hormone is produced mainly in the blood during the cleavage of angiotensin I by angiotensin converting enzyme (ACE) localized on the endothelium of blood vessels of lung, kidney, and many other organs, and is the end product of the RAS. AII is a powerful arterial vasoconstricter that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by the partial agonist activity and lack of oral absorption [M. Antonaccio. *Clin. Exp. Hypertens.* A4, 27–46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; 4,582,847; and 4,880,804; in European Patent Applications 028,834; 245,637; 253,310; and 291,969; and in articles by A. T. Chiu, et al. [*Eur. J. Pharm. Exp. Therap,* 157, 13–21 (1988)] and by P. C. Wong, et al. [*J. Pharm. Exp. Therap,* 247, 1–7 (1988)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

Imidazo[4,5-b]pyridines have been disclosed by Merck & Co., I.C.I., Takeda and Eisai in following European Patent Publications: 400,974; 399,731; 434,038; 549,136 and 420,237, respectively. The compounds disclosed in the above-cited applications, with the exception of EP 400,974, do not disclose 6-amino-3H-imidazo[4,5-b]pyridines bearing a biphenyl substituent substituted with a sulfonyl group. The compounds of the present invention are encompassed within the genus of EP 400,974, which is substantially the same as U.S. Ser. No. 07/516,286 filed on May 5, 1990.

DETAILED DESCRIPTION OF THE INVENTION

This invention relates to 6-amino substituted imidazo[4,5-b]pyridines of the structural formula I shown below which are angiotensin II antagonists and are useful in the treatment of hypertension, congestive heart failure, and elevated intraocular pressure

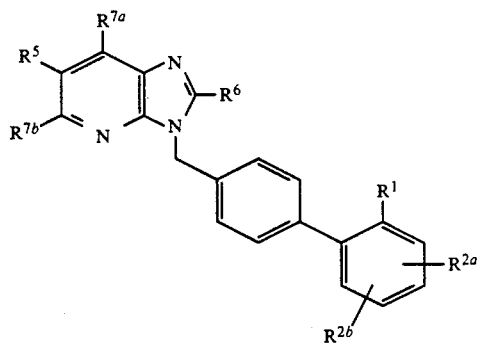

or a pharmaceutically acceptable salt thereof wherein:
$R^1$ is:
(a) —$SO_2NHC(O)R^{23}$,
(b) —$SO_2NHC(O)NR^4R^{23}$, or
(c) —$SO_2NHC(O)N[CH_2CH_2]_2O$;

$R^{2a}$ and $R^{2b}$ are independently:
(a) H,
(b) Cl, Br, I, F,
(c) $C_1$–$C_6$-alkyl, substituted or unsubstituted with aryl, furyl, thienyl, pyridyl, $C_3$–$C_6$-cycloalkyl, F, $C_1$–$C_3$-alkoxy, polyfluoro-$C_1$–$C_4$-alkyl, morpholine, pyrrolidine, and —$N(R^4)(R^{23})$,
(d) $C_1$–$C_6$-alkoxy, unsubstituted or substituted with F and polyfluoro-$C_1$–$C_4$-alkyl,
(e) $C_1$–$C_6$-alkoxyalkyl, or
(f) aryl;
wherein aryl is phenyl or naphthyl substituted or unsubstituted with one or two substituents selected from the group consisting of Cl, Br, I, F, $C_1$–$C_4$-alkyl, $C_1$–$C_4$-alkoxy, $CF_3$, $C_1$–$C_4$-alkylthio, OH, NH($C_1$–$C_4$-alkyl), N($C_1$–$C_4$-alkyl)$_2$, $CO_2H$, and $CO_2$-$C_1$–$C_4$-alkyl;

$R^4$ is:
(a) H,
(b) aryl, wherein aryl is as defined above, or
(c) $C_1$–$C_6$-alkyl, substituted or unsubstituted with aryl, furyl, thienyl, pyridyl, $C_3$–$C_6$-cycloalkyl, and F;

R4a is:
(a) H,
(b) aryl, wherein aryl is as defined above, or
(c) $C_1$–$C_6$-alkyl, substituted or unsubstituted with aryl, furyl, thienyl, pyridyl, $C_3$–$C_6$-cycloalkyl, and F;

$R^5$ is:
(a) —$NH_2$,
(b) —$N(R^4)R^{23}$,
(c) —$N(R^4)COR^{23}$,
(d) —$N(R^4)(C_3$–$C_7$-cycloalkyl), (e)

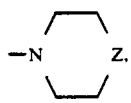

(f) —NHSO$_2$CF$_3$,
(g) —NHSO$_2$R$^{23}$,
(h) —NHSO$_2$NHR$^{23}$,
(i) —NHSO$_2$NHCOR$^{23}$,
(j) —NHSO$_2$NHSO$_2$R$^{23}$,
(k) —N(R$^4$)CO$_2$R$^{23}$,
(l) —N(R$^4$)CON(R$^4$)(R$^{23}$),
(m)

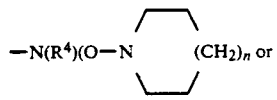

(n)

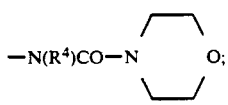

n is: 0, 1 or 2;
Z is:
  (a) (CH$_2$)n,
  (b) NR$^4$,
  (c) NCOR$^{23}$,
  (d) NCO$_2$R$^{23}$,
  (e) NSO$_2$R$^{23}$, or
  (f) O ;
R$^6$ is:
  (a) C$_1$-C$_9$-alkyl, C$_2$-C$_6$-alkenyl or C$_2$-C$_6$-alkynyl, which is substituted or unsubstituted with a substituent selected from the group consisting of: aryl as defined above, C$_3$-C$_7$-cycloalkyl, Cl, Br, I, F, —CF$_2$CF$_3$, —N(C$_1$-C$_4$-alkyl)$_2$, —CF$_3$, —CF$_2$CH$_3$, C$_1$-C$_4$-alkoxy; or
  (b) polyfluoro-C$_1$-C$_4$-alkyl,
  (c) C$_3$-C$_7$-cycloalkyl, unsubstituted or substituted with one or two substituents selected from the group consisting of: C$_1$-C$_4$-alkyl or —CF$_3$ or
  (d) C$_1$-C$_6$-alkyloxy;
R$^{7a}$ and R$^{7b}$ are independently:
  (a) H,
  (b) —C$_1$-C$_5$-alkyl,
  (c) —C$_1$-C$_5$-polyfluoroalkyl,
  (d) —C$_3$-C$_6$-cycloalkyl,
  (e) Cl, Br, I, F,
  (f) —O—C$_1$-C$_5$-alkyl,
  (g) —S—C$_1$-C$_5$-alkyl,
  (h) —CO$_2$R$^4$, or
  (i) —CON(R$^4$)(R$^{23}$);
R$^{23}$ is:
  (a) aryl as defined above,
  (b) heteroaryl as defined below,
  (c) C$_3$-C$_6$-cycloalkyl,
  (d) C$_1$-C$_7$-alkyl which can be optionally substituted with a substituent that is a member selected from the group consisting of: aryl as defined above, heteroaryl as defined above, —C$_3$-C$_7$-cycloalkyl, —O(C$_3$-C$_7$-cycloalkyl) —OH, —SH, —C$_1$-C$_4$-alkyl, —O(C$_1$-C$_4$-alkyl), —S(C$_1$-C$_4$-alkyl), —CF$_3$, Cl, Br, F, I, —CO$_2$H, —CO$_2$-C$_1$-C$_4$-alkyl, —NH$_2$, —NH(C$_1$-C$_4$-alkyl), —NHCOR$^{4a}$, —N(C$_1$-C$_4$-alkyl)$_2$, and —OC$_6$H$_5$— or
  (e) polyfluoro-C$_1$-C$_4$-alkyl; and wherein heteroaryl is defined as a 5- or 6-membered aromatic ring containing 1, 2 or 3 heteroatoms selected from the group consisting of O, N, and S.

The terms "alkyl," "alkenyl," "alkynyl," and the like include both the straight chain and branched chain species of these generic terms wherein the number of carbon atoms in the species permit. Unless otherwise noted, the specific names for these generic terms shall mean the straight chain species. For example, the term "butyl" shall means the normal butyl substituent, n-butyl.

The heteroaryl substituent recited above represents any 5- or 6-membered aromatic ring containing from one to three heteroatoms selected from the group consisting of nitrogen, oxygen, and sulfur, for example, pyridyl, thienyl, furyl, pyrazolyl, pyrrolyl, imidazolyl, pyridazinyl, pyrimidinyl, pyrazinyl, isoxazolyl, isothiazolyl, oxazolyl, triazolyl and thiazolyl.

An embodiment of the novel compounds of this invention is the class of compounds of Formula II

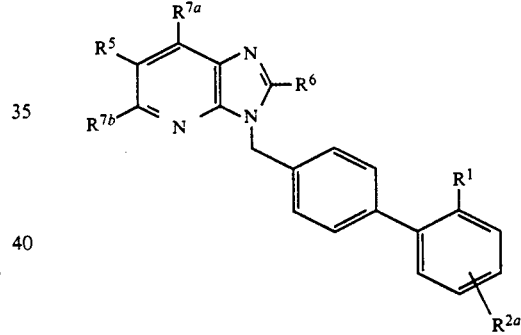

or a pharmaceutically acceptable salt thereof wherein:
R$^1$ is:
  (a) SO$_2$NHCOR$^{23}$, or
  (b) SO$_2$NHCONR$^4$R$^{23}$;
R$^{2a}$ is:
  (a) H, or
  (b) C$_1$-C$_6$-alkyl or C$_1$-C$_6$-alkoxy, unsubstituted or substituted with polyfluoro-C$_1$-C$_6$-alkyl;
R$^5$ is:
  (a) -N(R$^4$)COR$^{23}$,
  (b) -NHSO$_2$R$^{23}$,
  (c) -N(R$^4$)CO$_2$R$^{23}$,
  (d) -N(R$^4$)CON(R$^4$)R$^{23}$,
  (e)

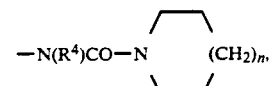

(f)

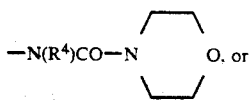

(g)

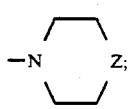

n is 0, 1, or 2;
Z is:
  (a) O,
  (b) NCOR$^{23}$,
  (c) NCO$_2$R$^{23}$,
  (d) NSO$_2$R$^{23}$, or
  (e) (CH$_2$)$_n$;
R$^{7a}$ and R$^{7b}$ are independently:
  (a) H,
  (b) C$_1$-C$_5$-alkyl, or
  (c) CO$_2$R$^4$;
and all other substituents are as defined above.

Tables A-F are subclasses of this embodiment, it should be understood that when (C5H9) and (C6H11) are used in the tables they represent cyclopentyl and cyclohexyl, respectively, and are representative compounds of the invention:

TABLE A

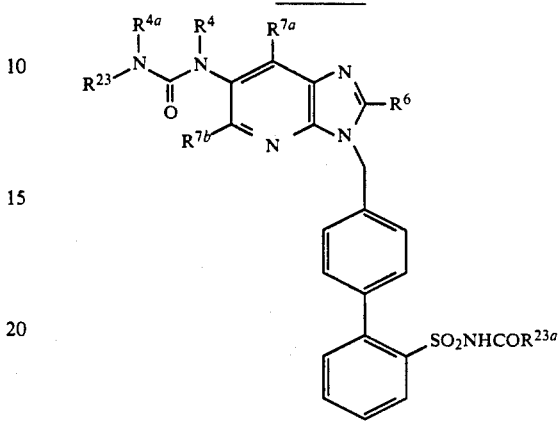

wherein:
R$^{7a}$ and R$^{7b}$ are independently: H or CH$_3$ and all other substitutents are as defined below:

| R$^6$ | NR$^{4a}$R$^{23}$ | R$^4$ | R$^{23a}$ |
|---|---|---|---|
| (CH$_2$)$_3$CH$_3$ | NHEt | H | (CH$_2$)$_2$CH$_3$ |
| (CH$_2$)$_3$CH$_3$ | NHEt | Me | (CH$_2$)$_3$CH$_3$ |
| (CH$_2$)$_3$CH$_3$ | NHEt | H | CH$_2$CH$_2$(C$_5$H$_9$) |
| (CH$_2$)$_3$CH$_3$ | NHEt | H | CH$_2$CH$_2$(C$_6$H$_5$) |
| (CH$_2$)$_3$CH$_3$ | NHEt | Me | CH$_2$CH$_2$(C$_6$H$_5$) |
| (CH$_2$)$_3$CH$_3$ | NHEt | H | CH$_2$CH$_2$OCH(CH$_3$)$_2$ |
| (CH$_2$)$_3$CH$_3$ | NHEt | H | CH$_2$O(C$_6$H$_5$) |
| (CH$_2$)$_3$CH$_3$ | NHEt | H | CH$_2$CH$_2$-thiophene-2-yl |
| (CH$_2$)$_3$CH$_3$ | NHEt | H | C$_6$H$_5$ |
| (CH$_2$)$_3$CH$_3$ | NHEt | H | 3,5-dimethylphenyl-1-yl |
| (CH$_2$)$_3$CH$_3$ | NHEt | H | 3,5-bis(trifluoromethyl)-phenyl-1-yl |
| (CH$_2$)$_2$CH$_3$ | NHEt | H | (CH$_2$)$_2$CH$_3$ |
| (CH$_2$)$_2$CH$_3$ | NHEt | Me | (CH$_2$)$_3$CH$_3$ |
| (CH$_2$)$_2$CH$_3$ | NHEt | H | CH$_2$CH$_2$(C$_5$H$_9$) |
| (CH$_2$)$_2$CH$_3$ | NHEt | H | CH$_2$CH$_2$(C$_6$H$_5$) |
| (CH$_2$)$_2$CH$_3$ | NHEt | Me | CH$_2$CH$_2$(C$_6$H$_5$) |
| (CH$_2$)$_2$CH$_3$ | NHEt | H | CH$_2$CH$_2$OCH(CH$_3$)$_2$ |
| (CH$_2$)$_2$CH$_3$ | NHEt | H | CH$_2$O(C$_6$H$_5$) |
| (CH$_2$)$_2$CH$_3$ | NHEt | H | CH$_2$CH$_2$-thiophene-2-yl |
| (CH$_2$)$_2$CH$_3$ | NHEt | H | C$_6$H$_5$ |
| (CH$_2$)$_2$CH$_3$ | NHEt | H | 3,5-dimethylphenyl-1-yl |
| (CH$_2$)$_2$CH$_3$ | NHEt | H | 3,5-bis(trifluoromethyl)-phenyl-1-yl |
| (CH$_2$)$_3$CH$_3$ | NHPr | H | (CH$_2$)$_2$CH$_3$ |
| (CH$_2$)$_3$CH$_3$ | NHPr | Me | (CH$_2$)$_3$CH$_3$ |
| (CH$_2$)$_3$CH$_3$ | NHPr | H | CH$_2$CH$_2$(C$_5$H$_9$) |
| (CH$_2$)$_3$CH$_3$ | NHPr | H | CH$_2$CH$_2$(C$_6$H$_5$) |
| (CH$_2$)$_3$CH$_3$ | NHPr | Me | CH$_2$CH$_2$(C$_6$H$_5$) |
| (CH$_2$)$_3$CH$_3$ | NHPr | H | CH$_2$CH$_2$OCH(CH$_3$)$_2$ |
| (CH$_2$)$_3$CH$_3$ | NHPr | H | CH$_2$O(C$_6$H$_5$) |
| (CH$_2$)$_3$CH$_3$ | NHPr | H | CH$_2$CH$_2$-thiophene-2-yl |
| (CH$_2$)$_3$CH$_3$ | NHPr | H | C$_6$H$_5$ |
| (CH$_2$)$_3$CH$_3$ | NHPr | H | 3,5-dimethylphenyl-1-yl |
| (CH$_2$)$_3$CH$_3$ | NHPr | H | 3,5-bis(trifluoromethyl)-phenyl-1-yl |
| (CH$_2$)$_2$CH$_3$ | NHPr | H | (CH$_2$)$_2$CH$_3$ |
| (CH$_2$)$_2$CH$_3$ | NHPr | Me | (CH$_2$)$_3$CH$_3$ |
| (CH$_2$)$_2$CH$_3$ | NHPr | H | CH$_2$CH$_2$(C$_5$H$_9$ ) |
| (CH$_2$)$_2$CH$_3$ | NHPr | H | CH$_2$CH$_2$(C$_6$H$_5$) |
| (CH$_2$)$_2$CH$_3$ | NHPr | Me | CH$_2$CH$_2$(C$_6$H$_5$) |
| (CH$_2$)$_2$CH$_3$ | NHPr | H | CH$_2$CH$_2$OCH(CH$_3$)$_2$ |
| (CH$_2$)$_2$CH$_3$ | NHPr | H | CH$_2$O(C$_6$H$_5$) |
| (CH$_2$)$_2$CH$_3$ | NHPr | H | CH$_2$CH$_2$-thiophene-2-yl |
| (CH$_2$)$_2$CH$_3$ | NHPr | H | C$_6$C$_5$ |
| (CH$_2$)$_2$CH$_3$ | NHPr | H | 3,5-dimethylphenyl-1-yl |
| (CH$_2$)$_2$CH$_3$ | NHPr | H | 3,5-bis(trifluoromethyl)- |

-continued

| R⁶ | NR⁴ᵃR²³ | R⁴ | R²³ᵃ |
|---|---|---|---|
| | | | phenyl-1-yl |
| (CH₂)₃CH₃ | N(CH₃)Pr | H | (CH₂)₂CH₃ |
| (CH₂)₃CH₃ | N(CH₃)Pr | Me | (CH₂)₃CH₃ |
| (CH₂)₃CH₃ | N(CH₃)Pr | H | CH₂CH₂(C₅H₉) |
| (CH₂)₃CH₃ | N(CH₃)Pr | H | CH₂CH₂(C₆H₅) |
| (CH₂)₃CH₃ | N(CH₃)Pr | Me | CH₂CH₂(C₆H₅) |
| (CH₂)₃CH₃ | N(CH₃)Pr | H | CH₂CH₂OCH(CH₃)₂ |
| (CH₂)₃CH₃ | N(CH₃)Pr | H | CH₂O(C₆H₅) |
| (CH₂)₃CH₃ | N(CH₃)Pr | H | CH₂CH₂-thiophene-2-yl |
| (CH₂)₃CH₃ | N(CH₃)Pr | H | C₆H₅ |
| (CH₂)₃CH₃ | N(CH₃)Pr | H | 3,5-dimethylphenyl-1-yl |
| (CH₂)₃CH₃ | N(CH₃)Pr | H | 3,5-bis(trifluoromethyl)-phenyl-1-yl |
| (CH₂)₂CH₃ | N(CH₃)Pr | H | (CH₂)₂CH₃ |
| (CH₂)₂CH₃ | N(CH₃)Pr | Me | (CH₂)₃CH₃ |
| (CH₂)₂CH₃ | N(CH₃)Pr | H | CH₂CH₂(C₅H₉) |
| (CH₂)₂CH₃ | N(CH₃)Pr | H | CH₂CH₂(C₆H₅) |
| (CH₂)₂CH₃ | N(CH₃)Pr | Me | CH₂CH₂(C₆H₅) |
| (CH₂)₂CH₃ | N(CH₃)Pr | H | CH₂CH₂OCH(CH₃)₂ |
| (CH₂)₂CH₃ | N(CH₃)Pr | H | CH₂O(C₆H₅) |
| (CH₂)₂CH₃ | N(CH₃)Pr | H | CH₂CH₂-thiophene-2-yl |
| (CH₂)₂CH₃ | N(CH₃)Pr | H | C₆H₅ |
| (CH₂)₂CH₃ | N(CH₃)Pr | H | 3,5-dimethylphenyl-1-yl |
| (CH₂)₂CH₃ | N(CH₃)Pr | H | 3,5-bis(trifluoromethyl)-phenyl-1-yl |
| (CH₂)₃CH₃ | NH-iso-Pr | H | (CH₂)₃CH₃ |
| (CH₂)₃CH₃ | NH-iso-Pr | H | CH₂CH₂(C₆H₅) |
| (CH₂)₂CH₃ | NH-iso-Pr | Me | (CH₂)₃CH₃ |
| (CH₂)₂CH₃ | NH-iso-Pr | H | CH₂CH₂(C₆H₅) |
| (CH₂)₃CH₃ | NH-iso-Pr | H | CH₂CH₂CH(CH₃)₂ |
| (CH₂)₃CH₃ | N(CH₃)-iso-Pr | H | (CH₂)₃CH₃ |
| (CH₂)₃CH₃ | N(CH₃)-iso-Pr | H | CH₂CH₂(C₆H₅) |
| (CH₂)₂CH₃ | N(CH₃)-iso-Pr | Me | (CH₂)₃CH₃ |
| (CH₂)₂CH₃ | N(CH₃)-iso-Pr | H | CH₂CH₂(C₆H₅) |
| (CH₂)₂CH₃ | N(CH₃)-iso-Pr | H | CH₂CH₂CH(CH₃)₂ |
| (CH₂)₂CH₃ | NH-iso-Pr | H | CH₂CH₂CH(CH₃)₂ | wherein:

R⁷ᵃ and R⁷ᵇ are independently: H or CH₃, and all other substitutents are as defined below:

TABLE B

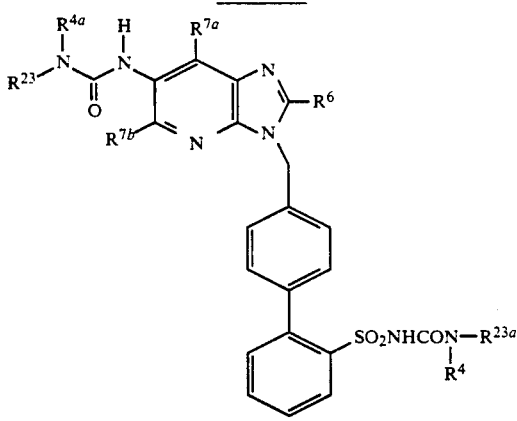

| R⁶ | NR⁴ᵃR²³ | NR⁴R²³ᵃ |
|---|---|---|
| (CH₂)₃CH₃ | NHEt | NH(CH₂)₃CH₃ |
| (CH₂)₃CH₃ | NHEt | NHCH₂CH(CH₃)₂ |
| (CH₂)₃CH₃ | NHEt | NH(CH₂)₂CH(CH₃)₂ |
| (CH₂)₃CH₃ | NHEt | NHCH₂(C₆H₅) |
| (CH₂)₃CH₃ | NHEt | N(CH₃)CH₂(C₆H₅) |
| (CH₂)₂CH₃ | NHEt | NH(CH₂)₃CH₃ |
| (CH₂)₂CH₃ | NHEt | NHCH₂CH(CH₃)₂ |
| (CH₂)₂CH₃ | NHEt | NH(CH₂)₂CH(CH₃)₂ |
| (CH₂)₂CH₃ | NHEt | NHCH₂(C₆H₅) |
| (CH₂)₂CH₃ | NHEt | N(CH₃)CH₂(C₆H₅) |
| (CH₂)₃CH₃ | NHPr | NH(CH₂)₃CH₃ |
| (CH₂)₃CH₃ | NHPr | NHCH₂CH(CH₃)₂ |
| (CH₂)₃CH₃ | NHPr | NH(CH₂)₂CH(CH₃)₂ |
| (CH₂)₃CH₃ | NHPr | NHCH₂(C₆H₅) |
| (CH₂)₃CH₃ | NHPr | N(CH₃)CH₂(C₆H₅) |

-continued

| $R^6$ | $NR^{4a}R^{23}$ | $NR^4R^{23a}$ |
|---|---|---|
| (CH$_2$)$_2$CH$_3$ | NHPr | NH(CH$_2$)$_3$CH$_3$ |
| (CH$_2$)$_2$CH$_3$ | NHPr | NHCH$_2$CH(CH$_3$)$_2$ |
| (CH$_2$)$_2$CH$_3$ | NHPr | NH(CH$_2$)$_2$CH(CH$_3$)$_2$ |
| (CH$_2$)$_2$CH$_3$ | NHPr | NHCH$_2$(C$_6$H$_5$) |
| (CH$_2$)$_2$CH$_3$ | NHPr | N(CH$_3$)CH$_2$(C$_6$H$_5$) |
| (CH$_2$)$_3$CH$_3$ | NH-iso-Pr | NH(CH$_2$)$_3$CH$_3$ |
| (CH$_2$)$_3$CH$_3$ | NH-iso-Pr | NHCH$_2$CH(CH$_3$)$_2$ |
| (CH$_2$)$_3$CH$_3$ | NH-iso-Pr | NH(CH$_2$)$_2$CH(CH$_3$)$_2$ |
| (CH$_2$)$_3$CH$_3$ | NH-iso-Pr | NHCH$_2$(C$_6$H$_5$) |
| (CH$_2$)$_3$CH$_3$ | NH-iso-Pr | N(CH$_3$)CH$_2$(C$_6$H$_5$) |
| (CH$_2$)$_2$CH$_3$ | NH-iso-Pr | NH(CH$_2$)$_3$CH$_3$ |
| (CH$_2$)$_2$CH$_3$ | NH-iso-Pr | NHCH$_2$CH(CH$_3$)$_2$ |
| (CH$_2$)$_2$CH$_3$ | NH-iso-Pr | NH(CH$_2$)$_2$CH(CH$_3$)$_2$ |
| (CH$_2$)$_2$CH$_3$ | NH-iso-Pr | NHCH$_2$(C$_6$H$_5$) |
| (CH$_2$)$_2$CH$_3$ | NH-iso-Pr | N(CH$_3$)CH$_2$(C$_6$H$_5$) |
| (CH$_2$)$_3$CH$_3$ | N(CH$_3$)-iso-Pr | NH(CH$_2$)$_3$CH$_3$ |
| (CH$_2$)$_3$CH$_3$ | N(CH$_3$)-iso-Pr | NHCH$_2$CH(CH$_3$)$_2$ |
| (CH$_2$)$_3$CH$_3$ | N(CH$_3$)-iso-Pr | NH(CH$_2$)$_2$CH(CH$_3$)$_2$ |
| (CH$_2$)$_3$CH$_3$ | N(CH$_3$)-iso-Pr | NHCH$_2$(C$_6$H$_5$) |
| (CH$_2$)$_3$CH$_3$ | N(CH$_3$)-iso-Pr | N(CH$_3$)CH$_2$(C$_6$H$_5$) |
| (CH$_2$)$_2$CH$_3$ | N(CH$_3$)-iso-Pr | NH(CH$_2$)$_3$CH$_3$ |
| (CH$_2$)$_2$CH$_3$ | N(CH$_3$)-iso-Pr | NHCH$_2$CH(CH$_3$)$_2$ |
| (CH$_2$)$_2$CH$_3$ | N(CH$_3$)-iso-Pr | NH(CH$_2$)$_2$CH(CH$_3$)$_2$ |
| (CH$_2$)$_2$CH$_3$ | N(CH$_3$)-iso-Pr | NHCH$_2$(C$_6$H$_5$) |
| (CH$_2$)$_2$CH$_3$ | N(CH$_3$)-iso-Pr | N(CH$_3$)CH$_2$(C$_6$H$_5$). |

TABLE C

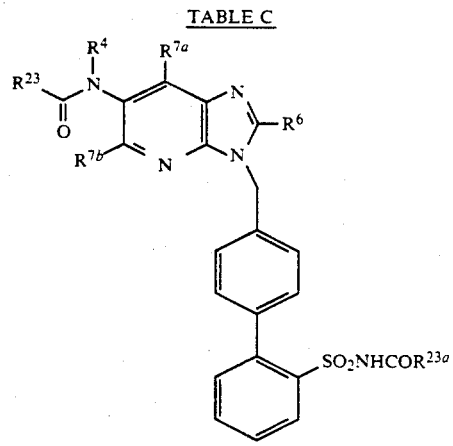

wherein:
$R^{7a}$ and $R^{7b}$ are independently: H or CH$_3$, and all other substitutents are as defined below:

| $R^6$ | $R^{23}$ | $R^4$ | $R^{23a}$ |
|---|---|---|---|
| (CH$_2$)$_3$CH$_3$ | (CH$_2$)$_3$CH$_3$ | H | (CH$_2$)$_2$CH$_3$ |
| (CH$_2$)$_3$CH$_3$ | (CH$_2$)$_3$CH$_3$ | H | (CH$_2$)$_3$CH$_3$ |
| (CH$_2$)$_3$CH$_3$ | (CH$_2$)$_3$CH$_3$ | Me | (CH$_2$)$_3$CH$_3$ |
| (CH$_2$)$_3$CH$_3$ | (CH$_2$)$_3$CH$_3$ | H | (CH$_2$)$_4$CH$_3$ |
| (CH$_2$)$_3$CH$_3$ | (CH$_2$)$_3$CH$_3$ | Me | (CH$_2$)$_4$CH$_3$ |
| (CH$_2$)$_3$CH$_3$ | (CH$_2$)$_3$CH$_3$ | H | (CH$_2$)$_5$CH$_3$ |
| (CH$_2$)$_3$CH$_3$ | (CH$_2$)$_3$CH$_3$ | H | CH$_2$CH(CH$_3$)$_2$ |
| (CH$_2$)$_3$CH$_3$ | (CH$_2$)$_3$CH$_3$ | H | CH$_2$CH$_2$CH(CH$_3$)$_2$ |
| (CH$_2$)$_3$CH$_3$ | (CH$_2$)$_3$CH$_3$ | H | CH$_2$CH(CH$_3$)CH(CH$_3$)$_2$ |
| (CH$_2$)$_3$CH$_3$ | (CH$_2$)$_3$CH$_3$ | H | CH$_2$(C$_5$H$_9$) |
| (CH$_2$)$_3$CH$_3$ | (CH$_2$)$_3$CH$_3$ | H | CH$_2$CH$_2$(C$_5$H$_9$) |
| (CH$_2$)$_3$CH$_3$ | (CH$_2$)$_3$CH$_3$ | H | CH$_2$(C$_6$H$_{11}$) |
| (CH$_2$)$_3$CH$_3$ | (CH$_2$)$_3$CH$_3$ | H | CH$_2$CH$_2$(C$_6$H$_{11}$) |
| (CH$_2$)$_3$CH$_3$ | (CH$_2$)$_3$CH$_3$ | H | CH$_2$(C$_6$H$_5$) |
| (CH$_2$)$_3$CH$_3$ | (CH$_2$)$_3$CH$_3$ | Me | CH$_2$(C$_6$H$_5$) |
| (CH$_2$)$_3$CH$_3$ | (CH$_2$)$_3$CH$_3$ | H | CH$_2$CH$_2$(C$_6$H$_5$) |
| (CH$_2$)$_3$CH$_3$ | (CH$_2$)$_3$CH$_3$ | Me | CH$_2$CH$_2$(C$_6$H$_5$) |
| (CH$_2$)$_3$CH$_3$ | (CH$_2$)$_3$CH$_3$ | H | CH(CH$_3$)CH$_2$CH$_3$ |
| (CH$_2$)$_3$CH$_3$ | (CH$_2$)$_3$CH$_3$ | H | CH(CH$_3$)CH$_2$CH$_2$CH$_3$ |
| (CH$_2$)$_3$CH$_3$ | (CH$_2$)$_3$CH$_3$ | H | C(CH$_3$)$_2$CH$_2$CH$_3$ |
| (CH$_2$)$_3$CH$_3$ | (CH$_2$)$_3$CH$_3$ | H | C(CH$_3$)$_2$CH$_2$CH$_2$CH$_3$ |
| (CH$_2$)$_3$CH$_3$ | (CH$_2$)$_3$CH$_3$ | H | CHC(CH$_3$)$_2$ |
| (CH$_2$)$_3$CH$_3$ | (CH$_2$)$_3$CH$_3$ | H | CH$_2$CHC(CH$_3$)$_2$ |
| (CH$_2$)$_3$CH$_3$ | (CH$_2$)$_3$CH$_3$ | H | CH$_2$CH$_2$OCH$_3$ |
| (CH$_2$)$_3$CH$_3$ | (CH$_2$)$_3$CH$_3$ | H | CH$_2$CH$_2$O(C$_6$H$_5$) |
| (CH$_2$)$_3$CH$_3$ | (CH$_2$)$_3$CH$_3$ | H | CH$_2$CH$_2$OCH$_2$CH$_3$ |

-continued

| $R^6$ | $R^{23}$ | $R^4$ | $R^{23a}$ |
|---|---|---|---|
| (CH$_2$)$_3$CH$_3$ | (CH$_2$)$_3$CH$_3$ | H | CH$_2$CH$_2$OCH(CH$_3$)$_2$ |
| (CH$_2$)$_3$CH$_3$ | (CH$_2$)$_3$CH$_3$ | H | CH$_2$OCH$_2$CH$_3$ |
| (CH$_2$)$_3$CH$_3$ | (CH$_2$)$_3$CH$_3$ | H | CH$_2$OCH$_2$(C$_6$H$_5$) |
| (CH$_2$)$_3$CH$_3$ | (CH$_2$)$_3$CH$_3$ | H | CH$_2$OCH(CH$_3$)$_2$ |
| (CH$_2$)$_3$CH$_3$ | (CH$_2$)$_3$CH$_3$ | H | CH$_2$OCH$_2$CH$_2$CH$_3$ |
| (CH$_2$)$_3$CH$_3$ | (CH$_2$)$_3$CH$_3$ | H | CH$_2$OCH$_2$CH(CH$_3$)$_2$ |
| (CH$_2$)$_3$CH$_3$ | (CH$_2$)$_3$CH$_3$ | H | CH$_2$O(C$_6$H$_5$) |
| (CH$_2$)$_3$CH$_3$ | (CH$_2$)$_3$CH$_3$ | H | CH$_2$O(C$_5$H$_9$) |
| (CH$_2$)$_3$CH$_3$ | (CH$_2$)$_3$CH$_3$ | H | CH$_2$OCH$_2$CH$_2$OCH$_3$ |
| (CH$_2$)$_3$CH$_3$ | (CH$_2$)$_3$CH$_3$ | H | CH$_2$CH$_2$-furan-2-yl |
| (CH$_2$)$_3$CH$_3$ | (CH$_2$)$_3$CH$_3$ | H | CH$_2$CH$_2$-furan-3-yl |
| (CH$_2$)$_3$CH$_3$ | (CH$_2$)$_3$CH$_3$ | H | CH$_2$CH$_2$-thiophene-2-yl |
| (CH$_2$)$_3$CH$_3$ | (CH$_2$)$_3$CH$_3$ | H | CH$_2$CH$_2$-thiophene-3-yl |
| (CH$_2$)$_3$CH$_3$ | (CH$_2$)$_3$CH$_3$ | H | cyclopropane |
| (CH$_2$)$_3$CH$_3$ | (CH$_2$)$_3$CH$_3$ | H | 2,2-dimethylcyclopropane-1-yl |
| (CH$_2$)$_3$CH$_3$ | (CH$_2$)$_3$CH$_3$ | H | C$_5$H$_9$ |
| (CH$_2$)$_3$CH$_3$ | (CH$_2$)$_3$CH$_3$ | H | C$_6$H$_{11}$ |
| (CH$_2$)$_3$CH$_3$ | (CH$_2$)$_3$CH$_3$ | H | C$_6$H$_5$ |
| (CH$_2$)$_3$CH$_3$ | (CH$_2$)$_3$CH$_3$ | H | 2-CH$_3$—C$_6$H$_4$ |
| (CH$_2$)$_3$CH$_3$ | (CH$_2$)$_3$CH$_3$ | H | 2-CH$_3$—C$_6$H$_4$ |
| (CH$_2$)$_3$CH$_3$ | (CH$_2$)$_3$CH$_3$ | H | 2-CF$_3$—C$_6$H$_4$ |
| (CH$_2$)$_3$CH$_3$ | (CH$_2$)$_3$CH$_3$ | H | 3-CH$_3$—C$_6$H$_4$ |
| (CH$_2$)$_3$CH$_3$ | (CH$_2$)$_3$CH$_3$ | H | 3-CH$_2$CH$_2$CH$_3$—C$_6$H$_4$ |
| (CH$_2$)$_3$CH$_3$ | (CH$_2$)$_3$CH$_3$ | H | 3-CF$_3$—C$_6$H$_4$ |
| (CH$_2$)$_3$CH$_3$ | (CH$_2$)$_3$CH$_3$ | H | 3,5-dimethylphenyl-1-yl |
| (CH$_2$)$_3$CH$_3$ | (CH$_2$)$_3$CH$_3$ | H | 3,5-bis(trifluoromethyl)phenyl-1-yl |
| (CH$_2$)$_3$CH$_3$ | (CH$_2$)$_3$CH$_3$ | H | furan-2-yl |
| (CH$_2$)$_3$CH$_3$ | (CH$_2$)$_3$CH$_3$ | H | furan-3-yl |
| (CH$_2$)$_3$CH$_3$ | (CH$_2$)$_3$CH$_3$ | H | thiophene-2-yl |
| (CH$_2$)$_3$CH$_3$ | (CH$_2$)$_3$CH$_3$ | H | thiophene-3-yl |
| (CH$_2$)$_3$CH$_3$ | (CH$_2$)$_3$CH$_3$ | H | 3-methylthiophene-2-yl |
| (CH$_2$)$_3$CH$_3$ | (CH$_2$)$_3$CH$_3$ | H | 3-chlorothiophene-2-yl |
| (CH$_2$)$_3$CH$_3$ | (CH$_2$)$_3$CH$_3$ | H | 3-bromothiophene-2-yl |
| (CH$_2$)$_3$CH$_3$ | (CH$_2$)$_3$CH$_3$ | H | 3-methylfuran-2-yl |
| (CH$_2$)$_3$CH$_3$ | (CH$_2$)$_3$CH$_3$ | H | 3-chlorofuran-2-yl |
| (CH$_2$)$_3$CH$_3$ | (CH$_2$)$_3$CH$_3$ | H | 3-bromofuran-2-yl |
| (CH$_2$)$_3$CH$_3$ | (CH$_2$)$_3$CH$_3$ | H | 4-propylphenyl |
| (CH$_2$)$_2$CH$_3$ | (CH$_2$)$_2$CH$_3$ | H | (CH$_2$)$_2$CH$_3$ |
| (CH$_2$)$_2$CH$_3$ | (CH$_2$)$_2$CH$_3$ | H | Butyl |
| (CH$_2$)$_2$CH$_3$ | (CH$_2$)$_2$CH$_3$ | Me | Butyl |
| (CH$_2$)$_2$CH$_3$ | (CH$_2$)$_2$CH$_3$ | H | $^n$Pentyl |
| (CH$_2$)$_2$CH$_3$ | (CH$_2$)$_2$CH$_3$ | H | $^n$Hexyl |
| (CH$_2$)$_2$CH$_3$ | (CH$_2$)$_2$CH$_3$ | H | CH$_2$CH(CH$_3$)$_2$ |
| (CH$_2$)$_2$CH$_3$ | (CH$_2$)$_2$CH$_3$ | H | CH$_2$CH$_2$CH(CH$_3$)$_2$ |
| (CH$_2$)$_2$CH$_3$ | (CH$_2$)$_2$CH$_3$ | H | CH$_2$CH(CH$_3$)CH(CH$_3$)$_2$ |
| (CH$_2$)$_2$CH$_3$ | (CH$_2$)$_2$CH$_3$ | H | CH$_2$(C$_5$H$_9$) |
| (CH$_2$)$_2$CH$_3$ | (CH$_2$)$_2$CH$_3$ | H | CH$_2$CH$_2$(C$_5$H$_9$) |
| (CH$_2$)$_2$CH$_3$ | (CH$_2$)$_2$CH$_3$ | Me | CH$_2$CH$_2$(C$_5$H$_9$) |
| (CH$_2$)$_2$CH$_3$ | (CH$_2$)$_2$CH$_3$ | H | CH$_2$(C$_6$H$_{11}$) |
| (CH$_2$)$_2$CH$_3$ | (CH$_2$)$_2$CH$_3$ | H | CH$_2$CH$_2$(C$_6$H$_{11}$) |
| (CH$_2$)$_2$CH$_3$ | (CH$_2$)$_2$CH$_3$ | H | CH$_2$(C$_6$H$_5$) |
| (CH$_2$)$_2$CH$_3$ | (CH$_2$)$_2$CH$_3$ | H | CH$_2$CH$_2$(C$_6$H$_5$) |
| (CH$_2$)$_2$CH$_3$ | (CH$_2$)$_2$CH$_3$ | H | CH(CH$_3$)CH$_2$CH$_3$ |
| (CH$_2$)$_2$CH$_3$ | (CH$_2$)$_2$CH$_3$ | H | CH(CH$_3$)CH$_2$CH$_2$CH$_3$ |
| (CH$_2$)$_2$CH$_3$ | (CH$_2$)$_2$CH$_3$ | H | C(CH$_3$)$_2$CH$_2$CH$_3$ |
| (CH$_2$)$_2$CH$_3$ | (CH$_2$)$_2$CH$_3$ | H | C(CH$_3$)$_2$CH$_2$CH$_2$CH$_3$ |
| (CH$_2$)$_2$CH$_3$ | (CH$_2$)$_2$CH$_3$ | H | CHC(CH$_3$)$_2$ |
| (CH$_2$)$_2$CH$_3$ | (CH$_2$)$_2$CH$_3$ | H | CH$_2$CHC(CH$_3$)$_2$ |
| (CH$_2$)$_2$CH$_3$ | (CH$_2$)$_2$CH$_3$ | H | CH$_2$CH$_2$OCH$_3$ |
| (CH$_2$)$_2$CH$_3$ | (CH$_2$)$_2$CH$_3$ | H | CH$_2$CH$_2$O(C$_6$H$_5$) |
| (CH$_2$)$_2$CH$_3$ | (CH$_2$)$_2$CH$_3$ | H | CH$_2$CH$_2$OCH$_2$CH$_3$ |
| (CH$_2$)$_2$CH$_3$ | (CH$_2$)$_2$CH$_3$ | H | CH$_2$CH$_2$OCH(CH$_3$)$_2$ |
| (CH$_2$)$_2$CH$_3$ | (CH$_2$)$_2$CH$_3$ | H | CH$_2$OCH$_2$CH$_3$ |
| (CH$_2$)$_2$CH$_3$ | (CH$_2$)$_2$CH$_3$ | H | CH$_2$OCH$_2$(C$_6$H$_5$) |
| (CH$_2$)$_2$CH$_3$ | (CH$_2$)$_2$CH$_3$ | H | CH$_2$OCH(CH$_3$)$_2$ |
| (CH$_2$)$_2$CH$_3$ | (CH$_2$)$_2$CH$_3$ | H | CH$_2$OCH$_2$CH$_2$CH$_3$ |
| (CH$_2$)$_2$CH$_3$ | (CH$_2$)$_2$CH$_3$ | H | CH$_2$OCH$_2$CH(CH$_3$)$_2$ |
| (CH$_2$)$_2$CH$_3$ | (CH$_2$)$_2$CH$_3$ | H | CH$_2$O(C$_6$H$_5$) |
| (CH$_2$)$_2$CH$_3$ | (CH$_2$)$_2$CH$_3$ | H | CH$_2$O(C$_5$H$_9$) |
| (CH$_2$)$_2$CH$_3$ | (CH$_2$)$_2$CH$_3$ | H | CH$_2$OCH$_2$CH$_2$OCH$_3$ |
| (CH$_2$)$_2$CH$_3$ | (CH$_2$)$_2$CH$_3$ | H | CH$_2$CH$_2$-furan-2-yl |
| (CH$_2$)$_2$CH$_3$ | (CH$_2$)$_2$CH$_3$ | H | CH$_2$CH$_2$-furan-3-yl |
| (CH$_2$)$_2$CH$_3$ | (CH$_2$)$_2$CH$_3$ | H | CH$_2$CH$_2$-thiophene-2-yl |
| (CH$_2$)$_2$CH$_3$ | (CH$_2$)$_2$CH$_3$ | H | CH$_2$CH$_2$-thiophene-3-yl |
| (CH$_2$)$_2$CH$_3$ | (CH$_2$)$_2$CH$_3$ | H | cyclopropane |
| (CH$_2$)$_2$CH$_3$ | (CH$_2$)$_2$CH$_3$ | H | 2,2-dimethylcyclopropane-1-yl |
| (CH$_2$)$_2$CH$_3$ | (CH$_2$)$_2$CH$_3$ | H | C$_5$H$_9$ |
| (CH$_2$)$_2$CH$_3$ | (CH$_2$)$_2$CH$_3$ | H | C$_6$H$_{11}$ |

-continued

| R⁶ | R²³ | R⁴ | R²³ᵃ |
|---|---|---|---|
| (CH₂)₂CH₃ | (CH₂)₂CH₃ | H | C₆H₅ |
| (CH₂)₂CH₃ | (CH₂)₂CH₃ | H | 2-CH₃—C₆H₄ |
| (CH₂)₂CH₃ | (CH₂)₂CH₃ | H | 2-CH₃—C₆H₄ |
| (CH₂)₂CH₃ | (CH₂)₂CH₃ | H | 2-CF₃—C₆H₄ |
| (CH₂)₂CH₃ | (CH₂)₂CH₃ | H | 3-CH₃—C₆H₄ |
| (CH₂)₂CH₃ | (CH₂)₂CH₃ | H | 3-CH₂CH₂CH₃—C₆H₄ |
| (CH₂)₂CH₃ | (CH₂)₂CH₃ | H | 3-CF₃—C₆H₄ |
| (CH₂)₂CH₃ | (CH₂)₂CH₃ | H | 3-CF₃-5-CF₃—C₆H₃ |
| (CH₂)₂CH₃ | (CH₂)₂CH₃ | H | furan-2-yl |
| (CH₂)₂CH₃ | (CH₂)₂CH₃ | H | furan-3-yl |
| (CH₂)₂CH₃ | (CH₂)₂CH₃ | H | thiophene-2-yl |
| (CH₂)₂CH₃ | (CH₂)₂CH₃ | H | thiophene-3-yl |
| (CH₂)₂CH₃ | (CH₂)₂CH₃ | H | 3-methylthiophene-2-yl |
| (CH₂)₂CH₃ | (CH₂)₂CH₃ | H | 3-chlorothiophene-2-yl |
| (CH₂)₂CH₃ | (CH₂)₂CH₃ | H | 3-bromiothiophene-2-yl |
| (CH₂)₂CH₃ | (CH₂)₂CH₃ | H | 3-methylfuran-2-yl |
| (CH₂)₂CH₃ | (CH₂)₂CH₃ | H | 3-chlorofuran-2-yl |
| (CH₂)₂CH₃ | (CH₂)₂CH₃ | H | 3-bromofuran-2-yl |
| (CH₂)₂CH₃ | (CH₂)₂CH₃ | H | 4-propylphenyl. |

TABLE D

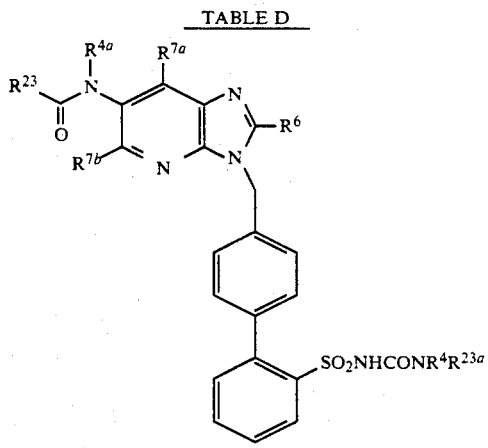

wherein:

$R^{7a}$ and $R^{7b}$ are independently: H or $CH_3$, and all other substitutents are as defined below:

| R⁶ | R²³ | R⁴ᵃ | NRR²³ᵃ |
|---|---|---|---|
| (CH₂)₃CH₃ | (CH₂)₃CH₃ | H | NH(CH₂)₂CH₃ |
| (CH₂)₃CH₃ | (CH₂)₃CH₃ | H | NH(CH₂)₃CH₃ |
| (CH₂)₃CH₃ | (CH₂)₃CH₃ | H | NH(CH₂)₄CH₃ |
| (CH₂)₃CH₃ | (CH₂)₃CH₃ | H | NHCH₂CH(CH₃)₂ |
| (CH₂)₃CH₃ | (CH₂)₃CH₃ | H | NH(CH₂)₂CH(CH₃)₂ |
| (CH₂)₃CH₃ | (CH₂)₃CH₃ | H | NHC₅H₉ |
| (CH₂)₃CH₃ | (CH₂)₃CH₃ | H | NHC₆H₁₁ |
| (CH₂)₃CH₃ | (CH₂)₃CH₃ | H | NHC₆H₅ |
| (CH₂)₃CH₃ | (CH₂)₃CH₃ | H | NH(3.5-dimethylphen-1-yl) |
| (CH₂)₃CH₃ | (CH₂)₃CH₃ | H | NHCH₂(C₆H₅) |
| (CH₂)₃CH₃ | (CH₂)₃CH₃ | H | NHCH₂-thiophene-2-yl |
| (CH₂)₃CH₃ | (CH₂)₃CH₃ | H | NHCH₂-thiophene-3-yl |
| (CH₂)₃CH₃ | (CH₂)₃CH₃ | H | NH₂(CH₂)₂OCH₃ |
| (CH₂)₃CH₃ | (CH₂)₃CH₃ | H | NH(CH₂)₂OCH(CH₃)₂ |
| (CH₂)₃CH₃ | (CH₂)₃CH₃ | H | morpholine-1-yl |
| (CH₂)₃CH₃ | (CH₂)₃CH₃ | H | N(CH₃)(CH₂)₃CH₃ |
| (CH₂)₃CH₃ | (CH₂)₃CH₃ | H | N(CH₃)C₆H₅ |
| (CH₂)₃CH₃ | (CH₂)₃CH₃ | H | N(CH₃)CH₂(C₆H₅) |
| (CH₂)₂CH₃ | (CH₂)₂CH₃ | H | NH(CH₂)₂CH₃ |
| (CH₂)₂CH₃ | (CH₂)₂CH₃ | H | NH(CH₂)₃CH₃ |
| (CH₂)₂CH₃ | (CH₂)₂CH₃ | H | NH(CH₂)₄CH₃ |
| (CH₂)₂CH₃ | (CH₂)₂CH₃ | H | NHCH₂CH(CH₃)₂ |
| (CH₂)₂CH₃ | (CH₂)₂CH₃ | H | NH(CH₂)₂CH(CH₃)₂ |
| (CH₂)₂CH₃ | (CH₂)₂CH₃ | H | NHC₅H₉ |
| (CH₂)₂CH₃ | (CH₂)₂CH₃ | H | NHC₆H₁₁ |
| (CH₂)₂CH₃ | (CH₂)₂CH₃ | H | NHC₆H₅ |
| (CH₂)₂CH₃ | (CH₂)₂CH₃ | H | NH(3.5-dimethylphen-1-yl) |
| (CH₂)₂CH₃ | (CH₂)₂CH₃ | H | NHCH₂(C₆H₅) |
| (CH₂)₂CH₃ | (CH₂)₂CH₃ | H | NHCH₂-thiophene-2-yl |
| (CH₂)₂CH₃ | (CH₂)₂CH₃ | H | NHCH₂-thiophene-3-yl |
| (CH₂)₂CH₃ | (CH₂)₂CH₃ | H | NH(CH₂)₂OCH₃ |
| (CH₂)₂CH₃ | (CH₂)₂CH₃ | H | NH(CH₂)₂OCH(CH₃)₂ |
| (CH₂)₂CH₃ | (CH₂)₂CH₃ | H | morpholine-1-yl |
| (CH₂)₂CH₃ | (CH₂)₂CH₃ | H | N(CH₃)(CH₂)₂CH₃ |
| (CH₂)₂CH₃ | (CH₂)₂CH₃ | H | N(CH₃)C₆H₅ |
| (CH₂)₂CH₃ | (CH₂)₂CH₃ | H | N(CH₃)CH₂(C₆H₅). |

TABLE E

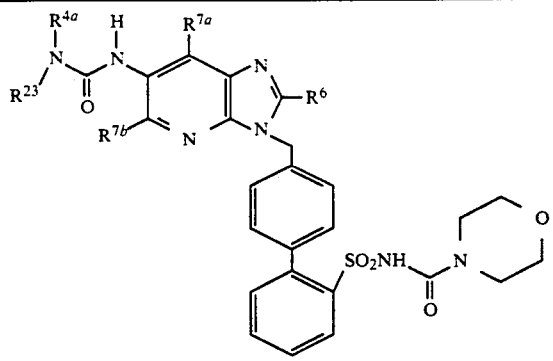

| $R^6$ | $NR^{4a}R^{23}$ | $R^{7a}$ | $R^{7b}$ |
|---|---|---|---|
| $(CH_2)_3CH_3$ | NHEt | H | H |
| $(CH_2)_3CH_3$ | NHEt | H | $CH_3$ |
| $(CH_2)_3CH_3$ | NHEt | $CH_3$ | H |
| $(CH_2)_3CH_3$ | NHEt | $CH_3$ | $CH_3$ |
| $(CH_2)_2CH_3$ | NHEt | H | H |
| $(CH_2)_2CH_3$ | NHEt | H | $CH_3$ |
| $(CH_2)_2CH_3$ | NHEt | $CH_3$ | H |
| $(CH_2)_2CH_3$ | NHEt | $CH_3$ | $CH_3$ |
| $(CH_2)_3CH_3$ | NHPr | H | H |
| $(CH_2)_3CH_3$ | NHPr | H | $CH_3$ |
| $(CH_2)_3CH_3$ | NHPr | $CH_3$ | H |
| $(CH_2)_3CH_3$ | NHPr | $CH_3$ | $CH_3$ |
| $(CH_2)_2CH_3$ | NHPr | H | H |
| $(CH_2)_2CH_3$ | NHPr | H | $CH_3$ |
| $(CH_2)_2CH_3$ | NHPr | $CH_3$ | H |
| $(CH_2)_2CH_3$ | NHPr | $CH_3$ | $CH_3$ |
| $(CH_2)_3CH_3$ | NH-iso-Pr | H | H |
| $(CH_2)_3CH_3$ | NH-iso-Pr | H | $CH_3$ |
| $(CH_2)_3CH_3$ | NH-iso-Pr | $CH_3$ | H |
| $(CH_2)_3CH_3$ | NH-iso-Pr | $CH_3$ | $CH_3$ |
| $(CH_2)_2CH_3$ | NH-iso-Pr | H | H |
| $(CH_2)_2CH_3$ | NH-iso-Pr | H | $CH_3$ |
| $(CH_2)_2CH_3$ | NH-iso-Pr | $CH_3$ | H |
| $(CH_2)_2CH_3$ | NH-iso-Pr | $CH_3$ | $CH_3$ |
| $(CH_2)_3CH_3$ | $N(CH_3)$-iso-Pr | H | H |
| $(CH_2)_3CH_3$ | $N(CH_3)$-iso-Pr | H | $CH_3$ |
| $(CH_2)_3CH_3$ | $N(CH_3)$-iso-Pr | $CH_3$ | H |
| $(CH_2)_3CH_3$ | $N(CH_3)$-iso-Pr | $CH_3$ | $CH_3$ |
| $(CH_2)_2CH_3$ | $N(CH_3)$-iso-Pr | H | H |
| $(CH_2)_2CH_3$ | $N(CH_3)$-iso-Pr | H | $CH_3$ |
| $(CH_2)_2CH_3$ | $N(CH_3)$-iso-Pr | $CH_3$ | H |
| $(CH_2)_2CH_3$ | $N(CH_3)$-iso-Pr | $CH_3$ | $CH_3$ |

TABLE F

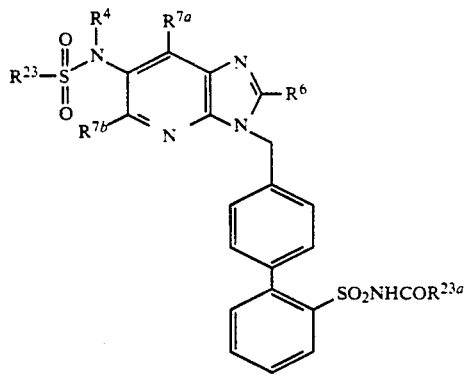

wherein:
$R^{7a}$ and $R^{7b}$ are independently: H or $CH_3$, and all other substitutents are as defined below:

| $R^6$ | $R^{23}$ | $R^4$ | $R^{23a}$ |
|---|---|---|---|
| $(CH_2)_3CH_3$ | Bu | H | $(CH_2)_3CH_3$ |
| $(CH_2)_3CH_3$ | Bu | H | $CH_2CH_2(C_6H_5)$ |
| $(CH_2)_3CH_3$ | Bu | Me | $(CH_2)_3CH_3$ |
| $(CH_2)_3CH_3$ | Bu | H | $CH_2CH_2(C_6H_5)$ |
| $(CH_2)_3CH_3$ | Bu | H | $CH_2CH_2CH(CH_3)_2$ |
| $(CH_2)_2CH_3$ | Bu | H | $(CH_2)_3CH_3$ |
| $(CH_2)_2CH_3$ | Bu | H | $CH_2CH_2(C_6H_5)$ |
| $(CH_2)_2CH_3$ | Bu | Me | $(CH_2)_2CH_3$ |
| $(CH_2)_2CH_3$ | Bu | H | $CH_2CH_2(C_6H_5)$ |
| $(CH_2)_2CH_3$ | Bu | H | $CH_2CH_2CH(CH_3)_2$ |

Another embodiment of this invention is the group of compounds of Formula III

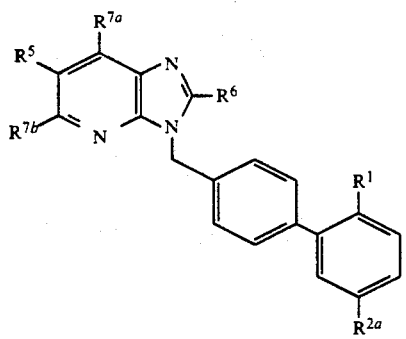

III or a pharmaceutically acceptable salt wherein:
R$^1$ is: -SO$_2$NHCOR$^{23}$ or -SO$_2$NHCONR$^4$R$^{23}$;
R$^{2a}$ is: H, -CH$_3$, -CH$_2$CH$_3$, -(CH$_2$)$_2$CH$_3$, -CH(CH$_3$)$_2$, -CH$_2$CH(CH$_3$)$_2$, -OCH$_2$CH$_3$, or -OCH$_2$CF$_3$;

R$^5$ is:
—N(R$^4$)COR$^{23}$,
—NHSO$_2$R$^{23}$,
—N(R$^4$)CO$_2$R$^{23}$,
—N(R$^4$)CON(R$^4$)R$^{23}$, or

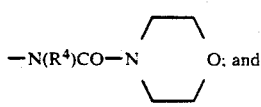

R$^6$ is: ethyl, propyl, butyl, cyclopropyl, ethyloxy or propyloxy.

TABLE G

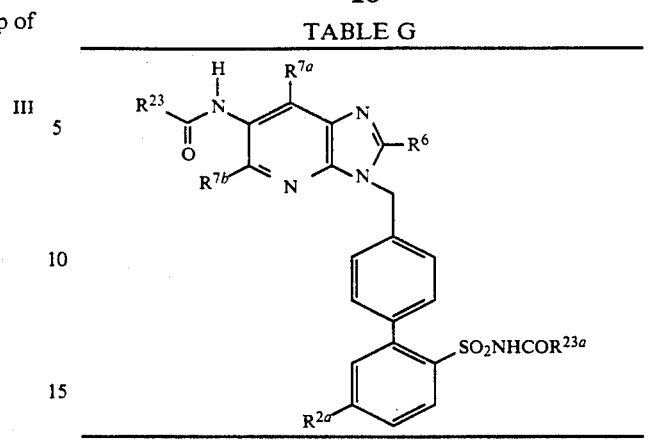

wherein:
R$^{7a}$ and R$^{7b}$ are independently: H or CH$_3$, and all other substitutents are as defined below:

| R$^6$ | R$^{23}$ | R$^{23a}$ | R$^{2a}$ |
|---|---|---|---|
| (CH$_2$)$_3$CH$_3$ | (CH$_2$)$_3$CH$_3$ | (CH$_2$)$_3$CH$_3$ | Pr |
| (CH$_2$)$_3$CH$_3$ | (CH$_2$)$_3$CH$_3$ | CH$_2$CH$_2$(C$_5$H$_9$) | Pr |
| (CH$_2$)$_3$CH$_3$ | (CH$_2$)$_3$CH$_3$ | CH$_2$CH$_2$OCH$_2$CH$_3$ | Pr |
| (CH$_2$)$_3$CH$_3$ | (CH$_2$)$_3$CH$_3$ | C$_6$H$_5$ | Pr |
| (CH$_2$)$_3$CH$_3$ | (CH$_2$)$_3$CH$_3$ | (CH$_2$)$_3$CH$_3$ | Et |
| (CH$_2$)$_3$CH$_3$ | (CH$_2$)$_3$CH$_3$ | CH$_2$CH$_2$(C$_5$H$_9$) | Et |
| (CH$_2$)$_3$CH$_3$ | (CH$_2$)$_3$CH$_3$ | CH$_2$CH$_2$OCH$_2$CH$_3$ | Et |
| (CH$_2$)$_3$CH$_3$ | (CH$_2$)$_3$CH$_3$ | C$_6$H$_5$ | Et |
| (CH$_2$)$_2$CH$_3$ | (CH$_2$)$_2$CH$_3$ | CH$_2$CH$_2$(C$_6$H$_5$) | Pr |
| (CH$_2$)$_2$CH$_3$ | (CH$_2$)$_2$CH$_3$ | CH$_2$CH$_2$(C$_6$H$_5$) | Et |
| (CH$_2$)$_2$CH$_3$ | (CH$_2$)$_2$CH$_3$ | (CH$_2$)$_3$CH$_3$ | Pr |
| (CH$_2$)$_2$CH$_3$ | (CH$_2$)$_2$CH$_3$ | (CH$_2$)$_3$CH$_3$ | Et |
| (CH$_2$)$_2$CH$_3$ | (CH$_2$)$_2$CH$_3$ | C$_6$H$_5$ | Pr |
| (CH$_2$)$_2$CH$_3$ | (CH$_2$)$_2$CH$_3$ | C$_6$H$_5$ | Et |
| (CH$_2$)$_3$CH$_3$ | (CH$_2$)$_3$CH$_3$ | CH$_2$CH$_2$OCH$_2$CH$_3$ | iso-Bu |
| (CH$_2$)$_3$CH$_3$ | (CH$_2$)$_3$CH$_3$ | (CH$_2$)$_3$CH$_3$ | iso-Bu |

TABLE H

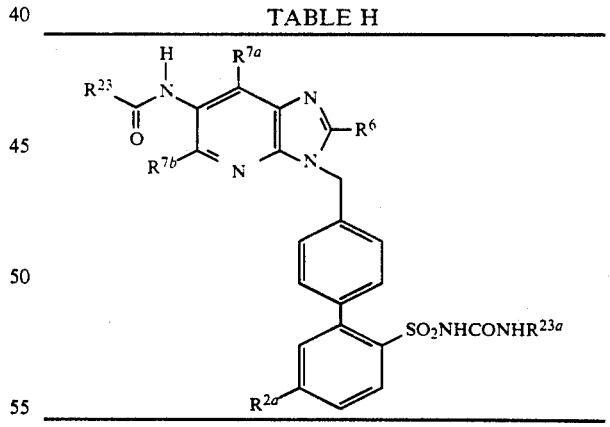

wherein:
R$^{7a}$ and R$^{7b}$ are independently: H or CH$_3$, and all other substitutents are as defined below:

| R$^6$ | R$^{23}$ | R$^{23a}$ | R$^{2a}$ |
|---|---|---|---|
| (CH$_2$)$_3$CH$_3$ | (CH$_2$)$_3$CH$_3$ | (CH$_2$)$_3$CH$_3$ | Pr |
| (CH$_2$)$_2$CH$_3$ | (CH$_2$)$_2$CH$_3$ | (CH$_2$)$_3$CH$_3$ | Pr |
| (CH$_2$)$_3$CH$_3$ | (CH$_2$)$_3$CH$_3$ | (CH$_2$)$_3$CH$_3$ | Et |
| (CH$_2$)$_2$CH$_3$ | (CH$_2$)$_2$CH$_3$ | (CH$_2$)$_3$CH$_3$ | Et |
| (CH$_2$)$_2$CH$_3$ | (CH$_2$)$_2$CH$_3$ | (CH$_2$)$_3$CH$_3$ | iso-Bu. |

TABLE I

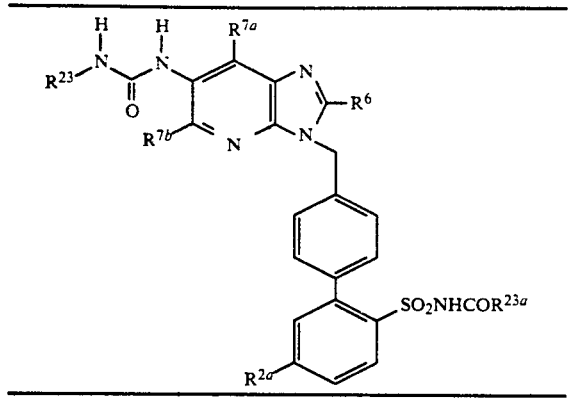

wherein:

$R^{7a}$ and $R^{7b}$ are independently: H or $CH_3$, and all other substitutents are as defined below:

| $R^6$ | $R^{23}$ | $R^{23a}$ | $R^{2a}$ |
|---|---|---|---|
| $CH_2CH_3$ | Et | $(CH_2)_3CH_3$ | Pr |
| $CH_2CH_3$ | $CH_3$ | $CH_2CH_2(C_5H_9)$ | Pr |
| $(CH_2)_3CH_3$ | iso-Pr | $(CH_2)_3CH_3$ | Pr |
| $CH_2CH_3$ | iso-Pr | $CH_2CH_2(C_5H_9)$ | Pr |
| $(CH_2)_2CH_3$ | iso-Pr | $(CH_2)_3CH_3$ | Pr |
| $CH_2CH_3$ | Et | $(CH_2)_3CH_3$ | Et |
| $CH_2CH_3$ | $CH_3$ | $CH_2CH_2(C_5H_9)$ | Et |
| $(CH_2)_3CH_3$ | iso-Pr | $(CH_2)_3CH_3$ | Et |
| $CH_2CH_3$ | iso-Pr | $CH_2CH_2(C_5H_9)$ | Et |
| $(CH_2)_2CH_3$ | iso-Pr | $(CH_2)_3CH_3$ | Et |
| $CH_2CH_3$ | Et | $(CH_2)_3CH_3$ | iso-Bu |
| $CH_2CH_3$ | $CH_3$ | $CH_2CH_2(C_5H_9)$ | iso-Bu |
| $(CH_2)_3CH_3$ | iso-Pr | $(CH_2)_3CH_3$ | iso-Bu |
| $CH_2CH_3$ | iso-Pr | $CH_2CH_2(C_5H_9)$ | iso-Bu |
| $(CH_2)_2CH_3$ | iso-Pr | $(CH_2)_3CH_3$ | iso-Bu. |

TABLE J

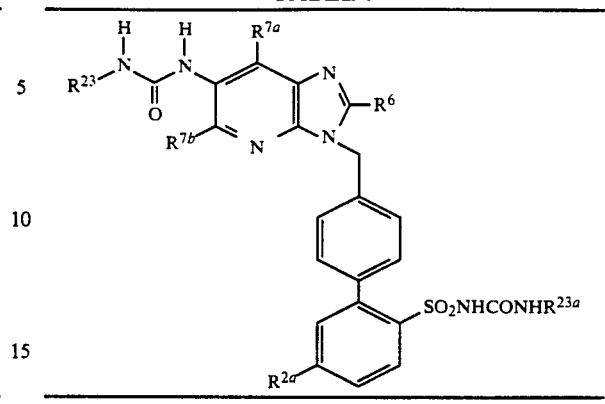

wherein:

$R^{7a}$ and $R^{7b}$ are independently: H or $CH_3$, and all other substitutents are as defined below:

| $R^6$ | $R^{23}$ | $R^{23a}$ | $R^{2a}$ |
|---|---|---|---|
| $(CH_2)_2CH_3$ | Et | $(CH_2)_3CH_3$ | Pr |
| $(CH_2)_2CH_3$ | Et | $(CH_2)_3CH_3$ | Pr |
| $CH_2CH_3$ | Et | $(CH_2)_3CH_3$ | Pr |
| $CH_2CH_3$ | $CH_3$ | $(CH_2)_3CH_3$ | Pr |
| $(CH_2)_3CH_3$ | iso-Pr | $(CH_2)_3CH_3$ | Pr |
| $CH_2CH_3$ | iso-Pr | $(CH_2)_3CH_3$ | Pr |
| $(CH_2)_2CH_3$ | Iso-Pr | $(CH_2)_3CH_3$ | Pr |
| $(CH_2)_2CH_3$ | Et | $(CH_2)_3CH_3$ | Et |
| $(CH_2)_3CH_3$ | Et | $(CH_2)_3CH_3$ | Et |
| $CH_2CH_3$ | Et | $(CH_2)_3CH_3$ | Et |
| $CH_2CH_3$ | $CH_3$ | $(CH_2)_3CH_3$ | Et |
| $(CH_2)_3CH_3$ | iso-Pr | $(CH_2)_3CH_3$ | Et |
| $CH_2CH_3$ | iso-Pr | $(CH_2)_3CH_3$ | Et |
| $(CH_2)_2CH_3$ | iso-Pr | $(CH_2)_3CH_3$ | Et |
| $(CH_2)_2CH_3$ | Et | $(CH_2)_3CH_3$ | iso-Bu |
| $(CH_2)_2CH_3$ | Et | $(CH_2)_3CH_3$ | iso-Bu |
| $CH_2CH_3$ | Et | $(CH_2)_3CH_3$ | iso-Bu |
| $CH_2CH_3$ | $CH_3$ | $(CH_2)_3CH_3$ | iso-Bu |
| $(CH_2)_3CH_3$ | iso-Pr | $(CH_2)_3CH_3$ | iso-Bu |
| $CH_2CH_3$ | iso-Pr | $(CH_2)_3CH_3$ | iso-Bu |
| $(CH_2)_2CH_3$ | iso-Pr | $(CH_2)_3CH_3$ | iso-Bu. |

The compounds of Formula (I) can be synthesized using the reactions and techniques described herein below. The reactions are performed in a solvent appropriate to the reagents and materials employed and suitable for the transformation being effected. It is understood by those skilled in the art of organic synthesis that the functionality present on the heterocycle and in the reactants being employed should be consistent with the chemical transformations being conducted. Depending

ABBREVIATIONS USED IN REACTION SCHEMES

| Reagents: | |
|---|---|
| NBS | N-bromosuccinimide |
| AIBN | Azo(bis)isobutyronitrile |
| DDQ | Dichlorodicyanoquinone |
| Ac$_2$O | acetic anhydride |
| TEA | triethylamine |
| DMAP | 4-dimethylaminopyridine |
| PPh$_3$ | triphenylphosphine |
| TFA | trifluoroacetic acid |
| TMS—Cl | trimethylsilyl chloride |
| Im | imidazole |
| AcSK | potassium thioacetate |
| P-TsOH | p-toluenesulfonic acid |

| Solvents: | |
|---|---|
| Et$_2$O | diethyl ether |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| DBU | 1,8-diazabicyclo-[5.4.0]undec-7-ene |
| Me$_3$SnCl | trimethylstannyl chloride |

| Others: | |
|---|---|
| rt | room temperature |
| TBDMS | t-butyldimethylsilyl |
| OTf | OSO$_2$CF$_3$ |
| OTs | OSO$_2$(4-methyl)phenyl |
| OMs | OSO$_2$CH$_3$ |
| Ph | phenyl |
| FAB-MS (FABMS) spectroscopy | Fast atom bombardment mass |
| NOE | Nuclear Overhauser Effect |
| SiO$_2$ | silica gel |
| trityl | triphenylmethyl |

As shown in Scheme 1, compounds of Formula I can be prepared by carrying out direct alkylation of alkali-metal salts of heterocycles (1) using appropriately protected benzyl halide, tosylate (OTs) or mesylate (OMs) derivatives (2). The salt is prepared preferably using MH (where M is lithium, sodium or potassium) is anhydrous dimethylformamide (DMF), or by treating it with a metal alkoxide such as sodium or potassium methoxide, ethoxide or t-butoxide in an appropriate alcohol such as methanol, ethanol or t-butanol as the solvent. The alkylation is generally carried out by dissolving the metal salt of the heterocycle in a dipolar aprotic solvent such as DMF or dimethylsulfoxide (DMSO) and reacting it with the alkylating agent at 20° C. to reflux temperature of the solvent for 1-24 hours.

SCHEME 1

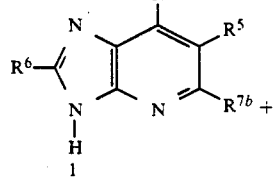

where Q=I, Br, Cl, -O-tosyl, or -O-mesyl.

If substituents and/or the hetero atom positions in the six-membered ring are not symetrically disposed, the alkylation on the imidazole nitrogen(s) generally produces a mixture of two regioisomers as products arising from N$^1$ and N$^3$ alkylation. These regioisomers I and Ia possess distinct physico-chemical and biological properties and in most cases can be separated and purified by using conventional separation techniques such as chromatography (flash column chromatography, medium-pressure liquid chromatography, high performance liquid chromatography) and/or crystallization. In those cases where separation of regioisomers is difficult by conventional techniques, the mixture can be transformed into suitable derivatives that can be separated by the above separation methods. The structural assignments of the isomers can be made using Nuclear Overhauser Effect (NOE), $^1$H-$^{13}$C coupled NMR experiments or X-ray crystallography.

When there is potential for alkylation on the $R^5$, $R^{7a}$, as $R^{7b}$ substituents, this can be avoided by the use of suitable protecting groups.

The heterocycles of type (1) can be prepared by any of the standard procedures described in the literature [J. A. Montgomery and J. A. Secrist III in "Comprehensive Heterocyclic Chemistry," Vol. 5, A. R. Katritsky and C. W. Rees Eds., Pergamon Press 1984; pp 567–597 and 631–656 and references cited therein]. As shown in Scheme 2, the most widely used starting materials: are the substituted 2,3-diaminopyridines (3). Fused imidazoles (4) can be prepared by condensation of (3) with an appropriate carboxylic acid, nitrile, imidate ester, or orthoesters, either neat, or in a solvent appropriate and compatible with the starting materials and reagents, such as polyphosphoric acid, ethanol, methanol, hydrocarbon solvents, and with a catalytic amount of acid if required.

SCHEME 2

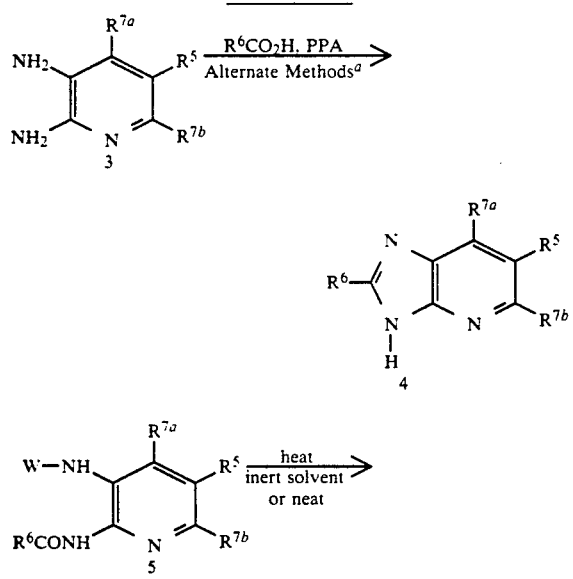

W = H or $R^6$CO $^a$ Alternate reagents and reaction conditions:
  $R^6$C≡N, PPA OC$_2$H$_5$
  $R^6$-C=NH•HCl, C$_2$H$_5$OH, Δ
  $R^6$C(OCH$_3$)$_3$, toluene, H$^+$, Δ
  $R^6$CHO, C$_2$H$_5$OH, Cu(OCOCH$_3$)$_2$.

A preferred method for preparing heterocycles of type 13 are shown in Schemes 3 and 4. Nitration of an appropriately substituted 2-amino-3-nitropyridine using nitric acid in sulfuric acid gives 2-amino-3,5-dinitropyridine derivative 6. Treatment of 6 under reducing conditions such as H$_2$ with a catalyst such as Raney-Nickel or palladium on carbon gives the 2,3,5-triaminopyridine derivative 7. Triamine 7 may be handled as the salt of an inorganic acid such as HCl or H$_3$PO$_4$. The salt may is preferentially prepared by the addition of the inorganic acid directly to the reduction step reaction mixture immediately after removal of the catalyst by vacuum filtration. Heating the triamine with 2 equivalents of an appropriate carboxylic acid in polyphosphoric acid provides 6-amidoimidazopyridine 8. Alternatively, this transformation may be performed using 2 equivalents of an appropriate acid chloride followed by heating in an aprotic solvent. The amide 8 may be hydrolysed to amine 9 by treatment with acid in water or alcoholic solvent. Treatment of amine 9 with an acid chloride provides analogs of 8, wherein $R^{23}$ is not equal to $R^6$. Additionally, treatment of amine 9 with an isocyanate or an alkylcarbamyl chloride in the presence of base affords the urea analog 10.

Imidazopyridines bearing an alkoxy group at the 2-position may be prepared as shown in Scheme 4. Heating triaminopyridine analogs 7 in the presence of excess tetraalkyl orthocarbonate affords imidazopyridines bearing a 6-carbamate substituent 11. Imidazopyridine analogs bearing 6-amino, 6-amido, and 6-ureido substituent are readily available from 11 by using the transformations outlined in the scheme.

SCHEME 3

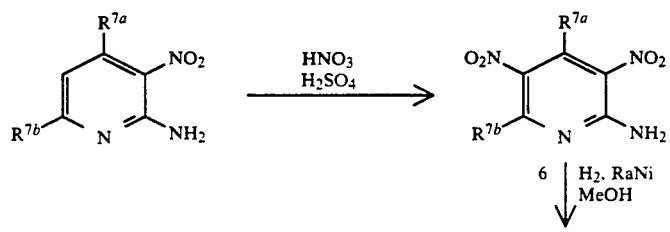

-continued
SCHEME 3
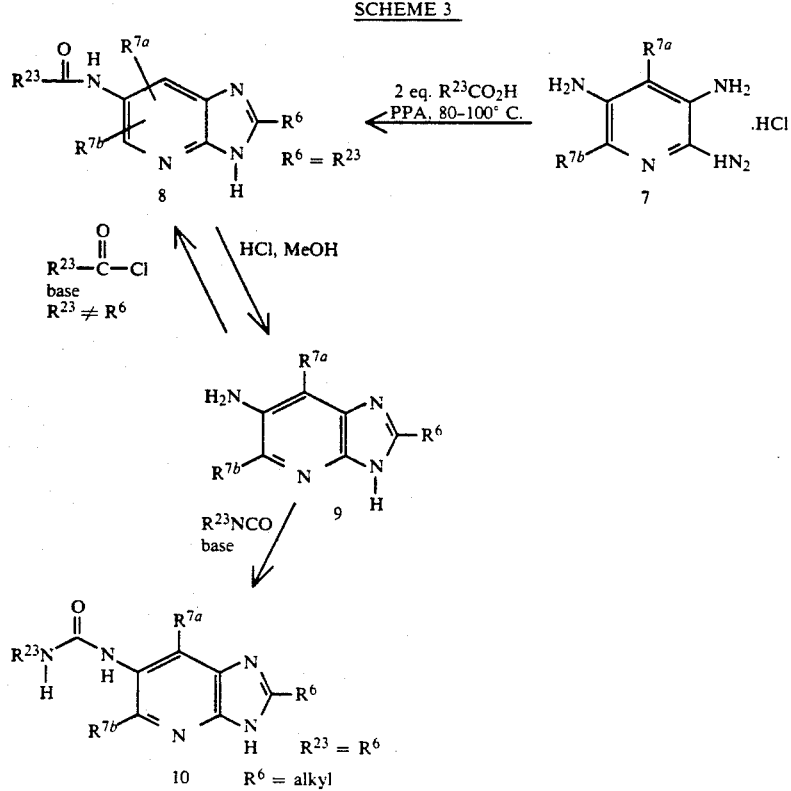
SCHEME 4
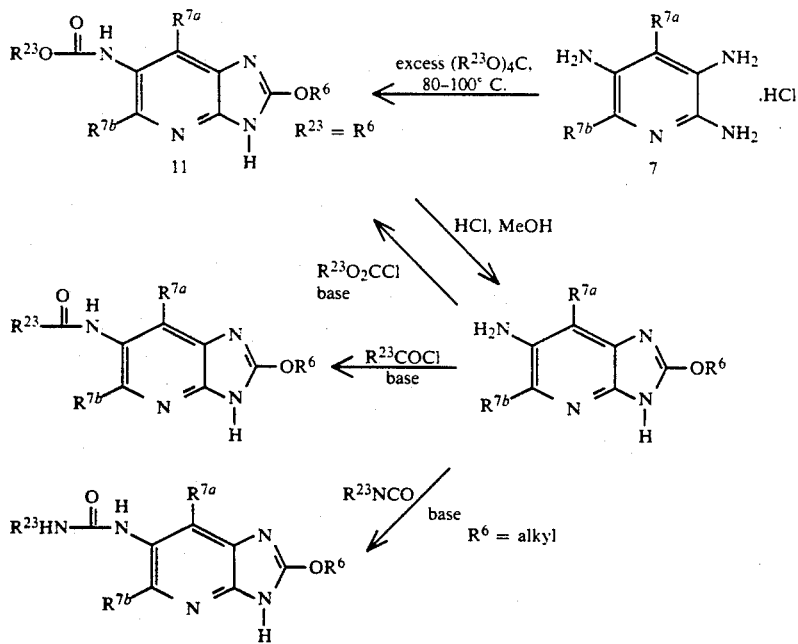

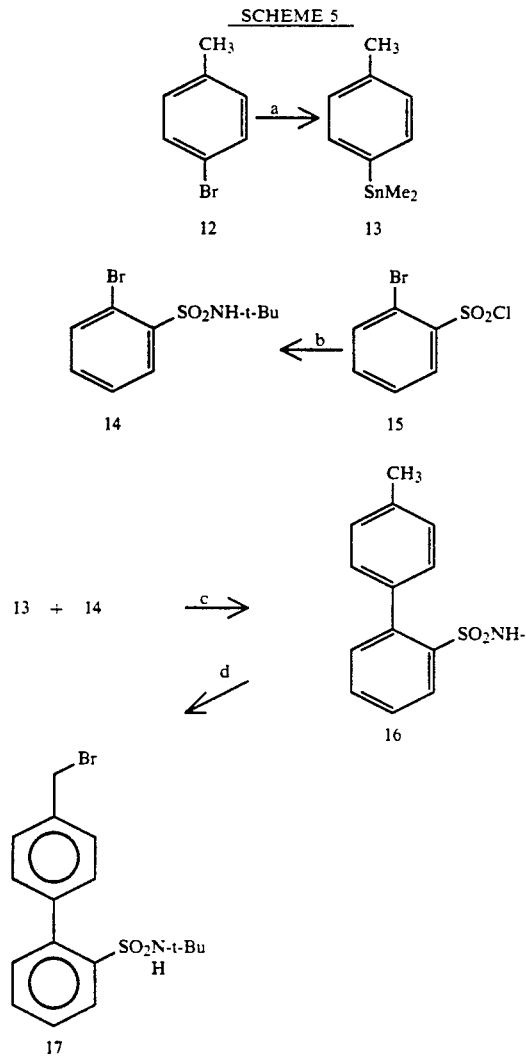

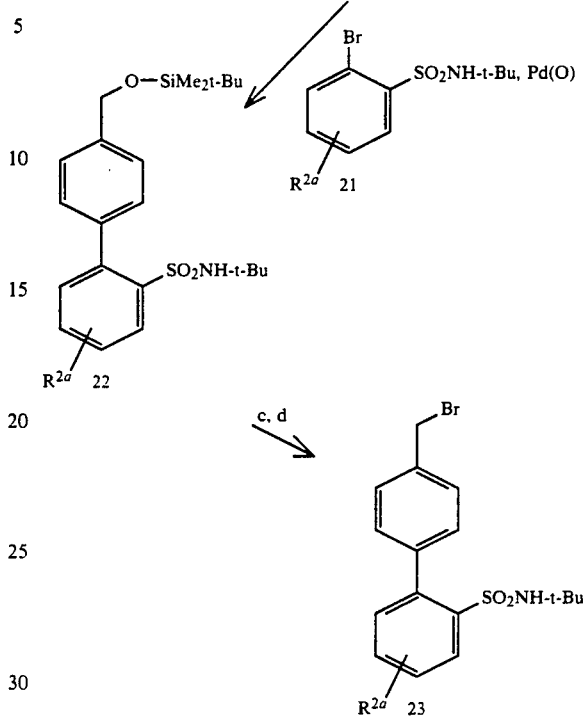

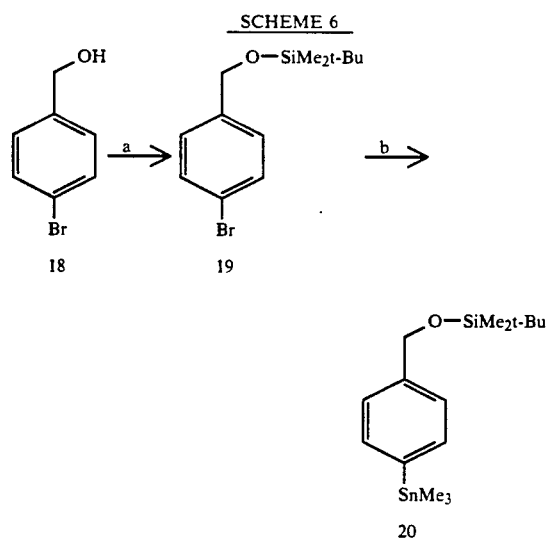

a t-BuMe₂Si—Cl/Imidazole, DMF
b t-BuLi, −78° C., Me₃SnCl
c Tetrabutylammonium fluoride
d CBr₄/Ph₃P.

The biaryl sulfonamides 16 can be prepared using palladium(0) catalyzed cross-coupling reactions of appropriate aryl-organotin precursors [J. K. Stille, Pure Appl. Chem., 57, 1771 (1985); T. R. Baiely, Tetra Lett., 27, 4407 (1986); D. A. Widdowson and Y. Z. Zhang, Tetrahedron, 42, 2111 (1986)], as outlined in Scheme 5. The organotin compound 13 [S. M. Moerlein, J. Organometallic Chem., 319, 29 (1987)], obtained from the aromatic precursor 12, may be coupled with the aryl sulfonamide 14 using Pd(PPh₃)₄ or (PPh₃)₂PdCl₂ as catalysts to give the biaryl sulfonamide 16. Benzylic bromination of 16 affords bromide 17. Similarly, the benzyl bromide 23 may be prepared from the appropriate organotin precursor 20 using the Pd(0) catalyzed cross-coupling reaction as outlined in Scheme 6.

Substituted imidazopyridines 25 are preferentially prepared by reaction of the heterocycle 24 with benzyl bromide 23 in the presence of base as outlined in Scheme 7. The t-butylsulfonamide 25 is deprotected using trifluoroacetic acid to form sulfonamide 26. Sulfonyl urea analogs 27 may be prepared by treatment of sulfonamide 26 with alkyl isocyanates or dialkylcarbamyl chlorides. Acylsulfonamide analogs 28 are prepared from intermediate sulfonamide 26 by treatment with an acyl chloride or an activated ester such as one derived from a carboxylic acid and carbonyl diimidazole.

SCHEME 7
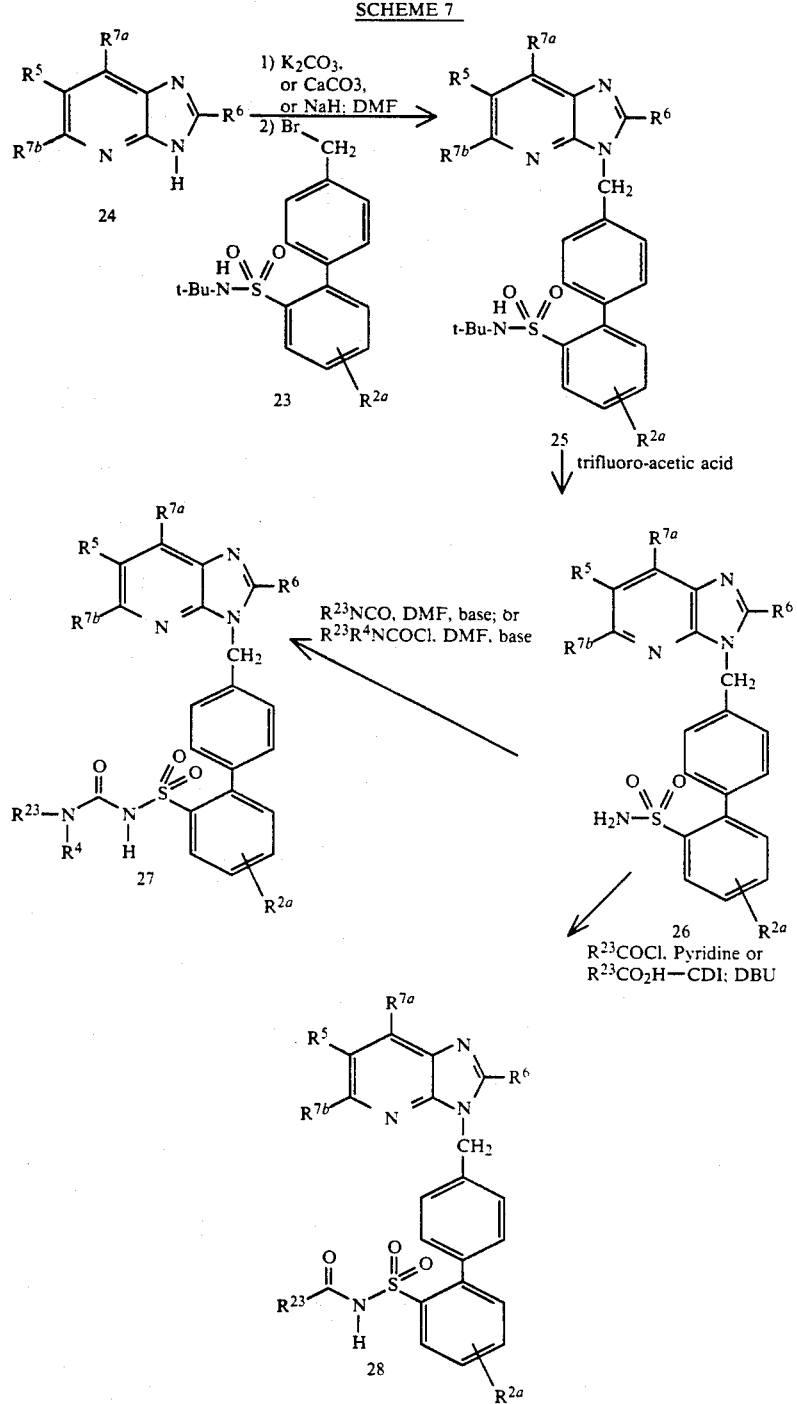
Chemical manipulation of the imidazopyridine-6-substituent may be performed at the unsubstituted stage ($R^{50}$=H) or at the 3-substituted stage of 29 as shown in Scheme 8.
SCHEME 8
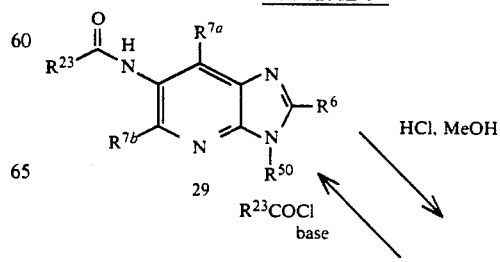

-continued
SCHEME 8

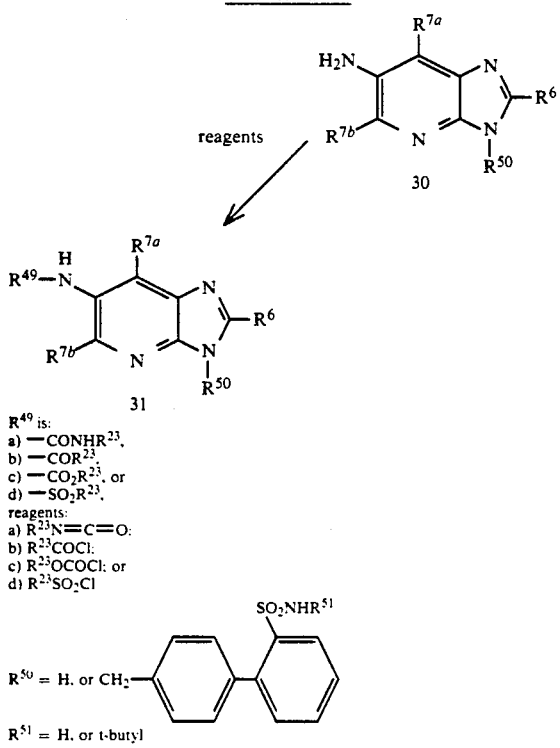

$R^{49}$ is:
a) —CONHR$^{23}$,
b) —COR$^{23}$,
c) —CO$_2$R$^{23}$, or
d) —SO$_2$R$^{23}$.
reagents:
a) R$^{23}$N=C=O;
b) R$^{23}$COCl;
c) R$^{23}$OCOCl; or
d) R$^{23}$SO$_2$Cl $R^{50}$ = H, or CH$_2$—

$R^{51}$ = H, or t-butyl

It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula I.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, H$_2$SO$_4$, H$_3$PO$_4$, methane-sulfonic, toluene-sulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the AT$_1$ and AT$_2$ receptors. In order to identify AII antagonists and determine their efficacy in vitro, the following ligand-receptor binding assays were used along with binding assays reported in the literature (R. S. Chang et al, Biochem. Biophys. Res. Commun. 1990, 171, 813.).

Receptor binding assay using rabbit aortae membrane preparation

Three frozen rabbit aortae (obtained from Pel-Freeze Biologicals) were suspended in 5 mM Tris-0.25M Sucrose, pH 7.4 buffer (50 ml) homogenized, and then centrifuged. The mixture was filtered through a cheesecloth and the supernatant was centrifuged for 30 minutes at 20,000 rpm at 4° C. The pellet thus obtained was resuspended in 30 ml of 50 mM Tris-5 mM MgCl$_2$ buffer containing 0.2 mg/ml Bacitration and the suspension was used for 100 assay tubes. Samples tested for screening were done in duplicate. To the membrane preparation (0.25 ml) there was added $^{125}$I-Sar$^1$Ile$^8$-angiotensin II [obtained from New England Nuclear] (10 ul; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration (IC$_{50}$) of potential AII antagonist which gives 50% displacement of the total specifically bound $^{125}$I-Sar$^1$Ile$^8$-angiotensin II was presented as a measure of the efficacy of such compounds as AII antagonists.

Receptor assay using Bovine adrenal cortex preparation

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [Na$_2$HPO$_4$ (10 mM)-NaCl (120 mM)-disodium EDTA (5 mM) containing phenylmethane sulfonyl fluoride (PMSF)(0.1 mM)]. (For screening of compounds, generally duplicates of tubes are used). To the membrane preparation (0.5 ml) there was added 3H-angiotensin II (50 mM) (10 ul) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration (IC$_{50}$) of potential AII antagonist which gives 50% displacement of the total specifically bound $^3$H-angiotensin II was presented as a measure of the efficacy of such compounds as AII antagonists.

Receptor assay using rat brain membrane preparation

Membranes from rat brain (thalamus, hypothamus and midbrain) are prepared by homogenization in 50 mM Tris HCl (pH 7.4), and centrifuged at 50,000× g. The resulting pellets are washed twice in 100 mM NaCl, 5 mM Na$_2$•EDTA, 10 mM Na$_2$HPO$_4$ (pH 7.4) and 0.1 mM PMSF by resuspension and centrifugation. For binding assays, the pellets are resuspended in 160 volumes of binding assay buffer (100 mM NaCl, 10 mM Na$_2$HPO$_4$, 5 mM Na$_2$•EDTA, pH 7.4, 0.1 mM PMSF, 0.2 mg/ml soybean trypsin inhibitor, 0.018 mg/ml o-phenanthroline, 77 mg/ml dithiothreitol and 0.14 mg/ml bacitracin. For $^{125}$I.Ile$^8$-angiotensin II binding assays, 10 µl of solvent (for total binding), Sar$^1$,Ile$^8$-angiotensin II (1 µM) (for nonspecific binding) or test compounds (for displacement) and 10 µl of [$^{125}$I]Sar$^1$,Ile$^8$-angiotensin II (23–46 pM) are added to duplicate tubes. The receptor membrane preparation (500 µl) is added to each tube to initiate the binding reaction. The reaction mixtures are incubated at 37° C. for 90 minutes. The reaction is then terminated by filtration under reduced pressure through glass-fiber GF/B filters and washed immediately 4 times with 4 ml of 5 mM ice-cold Tris HCl (pH 7.6) containing 0.15M NaCl. The radioactivity trapped on the filters is counted using a gamma counter.

The antihypertensive effects of the compounds described in the present invention may be evaluated using the methodology described below: Male Charles River Sprague-Dawley rats (300–375 gm) were anesthetized with methohexital (Brevital; 50 mg/kg i.p.) and the trachea was cannulated with PE 205 tubing. A stainless steel pithing rod (1.5 mm thick, 150 mm long) was inserted into the orbit of the right eye and down th spinal column. The rats were immediately placed on a Harvard Rodent Ventilator (rate-60 strokes per minute, volumn-1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later angiotensin II or other agonists were administered intravenously at 30-minute intervals and the increase in the diastolic blood pressure was recorded before and after drug or vehicle administration.

Using the methodology described above, representative compounds of this invention were evaluated and were found to exhibit an activity of at least IC$_{50}$<50 µM, in both the AT$_1$ and AT$_2$ angiotensin II receptor subtypes, thereby demonstrating and confirming the utility of the compounds of the invention as effective A II antagonists.

The compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperclasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Perferably, the dosage range will be about 2.5 to 250 mg. per patient per day; more preferably about 5 to 150 mg. per patient per day.

The compounds of this invention can also be administered in combination with other antihypertensives and-/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the unit dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples further illustrate the preparation of the compounds of Formula I and their incorporation into pharmaceutical compositions and, as such, are not be considered or construed as limiting the invention recited in the appended claims.

Example 1

2-butyl-3-[[2'-[[(3-cyclopentyl-1-oxopropyl)amino]-sulfonyl][1,1'-biphenyl]-4-yl]methyl]-6-[(1-oxopentyl)-amino]-3H-imidazo[4,5-b]pyridine Step 1: Preparation of 2-amino-3,5-dinitropyridine To a stirred solution of 2-amino-3-nitropyridine (8.74 g, 63 mmol) in conc. $H_2SO_4$ (50 mL) at 0° C. was added $HNO_3$ (3.10 mL, d=1.49) drop-wise over 10 min. The mixture was warmed to r.t. for 20 min then heated to 50° C. for 90 min. The reaction mixture was cooled and poured into 400 g of ice. The resulting precipitate was filtered, washed with cold water, and air dried to give 2-amino-3,5-dinitropyridine as a yellow solid.

Step 2: Preparation of 2-butyl-6-[(1-oxopentyl)amino]-imidazo[4,5-b]pyridine

A mixture of 2-amino-3,5-dinitropyridine (5.32 g, 28.9 mmol), THF (100 mL), methanol (250 mL) and Raney-nickel (3 mL of a 1:1 suspension in $H_2O$) was stirred under $H_2$ (1 atm.) was stirred for 5 h. The reaction mixture was quickly filtered into a receiving flask containing 5 mL of conc. HCl and the solvent was removed in vacuo at r. t. To this crude 2,3,5-triaminopyridine.HCl was added valeric acid (9.43 mL, 86.7 mmol) and polyphosphoric acid (100 mL) and this mixture was heated to 95° C. for 6 h. The warmed mixture was poured into stirred ice-$H_2O$ (200 mL) and this mixture was cooled and neutralized (to pH 4) by the addition of conc. $NH_4OH$. Extraction with EtOAc(3×75 mL), concentration, and purification ($SiO_2$, 5% MeOH/EtOAc) gave the title compound as solid.

Step 3: Preparation of 2-butyl-3-[[2'-[[(1,1-dimethylethyl)amino]sulfonyl][1,1'-biphenyl]-4-yl]-methyl]-6-[(1-oxopentyl)amino]-3H-imidazo[4,5-b]pyridine A solution of 2-butyl-6-[(1-oxopentyl)amino]-imidazo[4,5-b]pyridine, $K_2CO_3$ (956 mg, 6.92 mmol), and 4'-bromomethylbiphenyl-2-tert-butylsulfonamide 1.65 g, 3.46 mmol) in DMF (15 mL) was stirred for 12 h at r.t. The reaction mixture was poured into $H_2O$ (50 mL), extracted with EtOAc (2×50 mL), concentrated, and purified ($SiO_2$, 4:1 EtOAc/hexanes) to give the title compound as a foam.

Step 4: Preparation of 2-butyl-3-[[2'-[aminosulfonyl]-[1,1'-biphenyl]-4-yl]methyl]-6-[(1-oxopentyl)-amino]-3H-imidazo[4,5-b]pyridine A solution of 2-butyl-3-[[2'-[[(1,1-dimethyl-ethyl)amino]sulfonyl][1,1'-biphenyl]-4-yl]methyl]-6-[(1-oxopentyl)amino]-3H-imidazo[4,5-b]pyridine (710 mg, 1.23 mmol) in trifluoroacetic acid (50 mL) was stirred at r. t. for 12 h. The mixture was concentrated, dissolved in EtOAc (40 mL) and washed with saturated aqueous $Na_2CO_3$. The organic extracts were dried ($K_2CO_3$) and concentrated to give the title compound as a solid.

Step 5: Preparation of 2-butyl-3-[[2'-[[(3-cyclopentyl-1-oxopropyl)amino]sulfonyl][1,1'-biphenyl]-4-yl]methyl]-6-[(1-oxopentyl)-amino]-3H-imidazo-[4,5-b]pyridine To a mixture of 2-butyl-3-[[2'-[[aminosulfonyl][1,1'-biphenyl]-4-yl]methyl]-6-[(1-oxopentyl)-amino]-3H-imidazo[4,5-b]-pyridine (88 mg, 0.169 mmol in pyridine (2.0 mL) was added 3-cyclopentylpropionyl chloride (0.10 mL). After 12 h at r. t., MeOH (2 mL) was added and the mixture was concentrated, dissolved in EtOAc (40 mL), washed sequentially with $H_2O$ (15 mL) and brine (15 mL), concentrated, and purified ($SiO_2$, (90; 9:1 $CH_2Cl_2$/MeOH/$NH_4OH$) to give the title compound as a solid.

$^1H$ NMR (200 MHz, 1:1 $CDCl_3/CD_3OD$) d 8.52 (d, 1H, J=2 Hz), 8.24 (d, 1H, J=2 Hz) 8.14 (dd, 1H, J=1.4 and 7.8 Hz), 7.55–7.39 (m, 2H), 7.32 (d, 2H, J=9 Hz), 7.18 (dd, 1H, J=1.4 and 6.0 Hz), 7.10 (d, 2H, J=9 Hz), 5.52 (s, 2H), 2.89 (t, 2H, J=7.4 Hz) 2.40 (t, 2H, J=7.2 Hz), 1.89–1.25 (m, 21H), 0.98–0.80 (m, 6H).

Example 2

The potassium salt of this AII antagonist and the other AII antagonists described in the examples were prepared by treatment with one molar equivalent of KOH in CH₃OH.

2-butyl-3-[[2'-[[(1-oxohexyl)amino]sulfonyl][1,1'-biphenyl]-4-yl]methyl]-6-[(1-oxopentyl)amino]-3H-imidazo]4,5-b]pyridine 2-Butyl-3-[[2'-[aminosulfonyl][1,1'-biphenyl]-4-yl]-methyl]-6-[(1-oxopentyl)amino]-3H-imidazo[4,5-b]-pyridine (85 mg, 0.162 mmol in pyridine (2.0 mL) was added hexanoyl chloride (0.23 mL). After 12 h at r. t., MeOH (2 mL) was added and the mixture was concentrated, dissolved in EtOAc (40 mL), washed sequentially with H₂O (15 mL) and brine (15 mL), concentrated, and purified (SiO₂, (93:3:4 CH₂Cl₂/MeOH/HOAc) to give the title compound as a solid.

¹H NMR (200 MHz, 1:1 CDCl₃/CD₃OD) d 8.55 (s, 1H, b), 8.21 (s, 1H, b), 8.19 (d, 1H) 7.62–7.43 (m, 2H), 7.30–7.15 (m, 3H) 7.15–7.03 (m, 2H) 5.52 (s, 2H), 2.87 (t, 2H) 2.38 (t, 2H), 1.90–0.80 (m, 25H).

Example 3

2-butyl-3-[[2'[[[(butylamino)carbonyl]amino]sulfonyl]-[1,1'-biphenyl]-4-yl]methyl-6-[(1-oxopentyl)amino]-3H-imidazo[4,5-b]pyridine To a mixture of 2-butyl-3-[[2'-[aminosulfonyl][1,1'-biphenyl]-4-yl]methyl]-6-[(1-oxopentyl)-amino]-3H-imidazo[4,5-b]-pyridine (59 mg, 0.113 mmol in DMF (0.3 mL) and triethylamine (0.3 mL) was added butylisocyanate (0.038 mL). After heating to 60° C. for 12 h, the mixture was cooled to r.t. and CH₂Cl₂ (50 mL) was added. Sequential washing with 5% aqueous citric acid (25 mL), and brine and evaporation of the organic layer gave a crude product which was further purified (SiO₂, (96:1.5:2 CH₂Cl₂/MeOH/HOAc) to give the title compound as a solid.

¹H NMR (200 MHz, 1:1 CDCl₃/CD₃OD) d 8.54 (s, 1H, b), 8.23 (s, 1H, b), 8.10 (d, 1H) 7.60–7.38 (m, 2H), 7.35–7.15 (m, 3H) 7.09 (d, 2H) 5.52 (s, 2H), 2.97–2.76 (m, 4H) 2.39 (t, 2H), 1.85–1.59 (m, 4H) 1.50–1.03 (m, 8H) 1.00–0.72 (m, 9H).

Example 4

2-butyl-3-[[2'-[[(2,2-diphenyl-1-oxoethyl)amino]-sulfonyl][1,1'-biphenyl]-4-yl]methyl]-7-methyl-6-[(1-oxopentyl)amino]-3H-imidazo[4,5-b]pyridine Step 1: Preparation of 2-amino-4-methyl-3,5-dinitropyridine To a stirred solution of 2-amino-4-methyl-3-nitropyridine (25.6 g, 167 mmol) in conc. H₂SO₄ (50 mL) at 0° C. was added HNO₃ (7.77 mL, d=1.49) drop-wise over 30 min. The mixture was warmed to r.t. for 1 h then heated to 50° C. for 60 min. The reaction mixture was cooled and poured into 500 g of ice. The resulting precipitate was filtered, washed with 50 mL of H₂O, and air dried to give 2-amino-4-methyl-3,5-dinitro-pyridine as a yellow solid.

Step 2: Preparation of 6-[(1-oxopentyl)amino]-2-butyl-7-methylimidazo[4,5-b]pyridine The title compound was prepared from 2-amino-4-methyl-3,5-dinitropyridine by a method similar to that described in Example 1, Step 2.

Step 3: Preparation of 2-butyl-3-[[2'-[[(1,1-dimethylethyl)amino]sulfonyl][1,1'-biphenyl]-4-yl]methyl]-7-methyl-6-[(1-oxopentyl)amino]-3H-imidazo[4,5-b]pyridine The title compound was prepared from 6-[(1-oxopentyl)amino]-2-butyl-7-methylimidazo[4,5-b]-pyridine as described in Example 1, Step 3.

Step 4: Preparation of 2-butyl-3-[[2'-[(amino)-sulfonyl][1,1'-biphenyl]-4-yl]methyl]-7-methyl-6-[(1-oxopentyl)amino]-3H-imidazo[4,5-b]pyridine The title compound was prepared from 2-Butyl-3-[[2'-[[(1,1-dimethylethyl)amino]sulfonyl][1,1'-biphenyl]-4-yl]methyl]-7-methyl-6-[(1-oxopentyl)-amino]-3H-imidazo[4,5-b]pyridine as described in Example 1, Step 4.

Step 5: Preparation of 2-butyl-3-[[2'-[[(2,2-diphenyl-1-oxoethyl)amino]sulfonyl][1,1'-biphenyl]-4-yl]methyl]-7-methyl-6-[(1-oxopentyl)amino]-3H-imidazo[4,5-b]pyridine The title compound was prepared from 2-butyl-3-[[2'-[(amino)sulfonyl][1,1'-biphenyl]-4-yl]methyl]-7-methyl-6-[(1-oxopentyl)amino]-3H-imidazo[4,5-b]pyridine and diphenylacetyl chloride as described in Example 1, Step 5.

¹H NMR (200 MHz, 1:1 CDCl₃/CD₃OD) d 8.25 (s, 1H), 8.20 (d, 1H) 7.55–7.38 (m, 3H), 7.15–6.70 (m, 14H), 5.52 (s, 2H), 4.49 (s, 1H), 2.86 (t, 2H), 2.55 (s, 3H), 2.41 (t, 2H), 1.81–1.60 (m, 4H) 1.52–1.30 (m, 4H) 1.03–0.85 (m, 6H).

Example 5

2-butyl-3-[[2'-[[(1-oxopentyl)amino]sulfonyl][1,1'-biphenyl]-4-yl]methyl]-5-methyl-6-[(1-oxopentyl)amino]-3H-imidazo[4,5-b]pyridine Step 1: Preparation of 2-amino-6-methyl-3,5-dinitropyridine To a stirred solution of 2-amino-6-methylpyridine (38 g, 352 mmol) in conc. H₂SO₄ (70 mL) at 0 ° C. was added HNO₃ (16.5 mL, d=1.49) drop-wise over 30 min. The mixture was warmed stirred an additional 1 h at 0° C. then poured into 500 g of ice. This heterogeneous mixture was stirred for 1 h at r.t., filtered, washed with 50 mL H₂O and the residue was briefly dried to give 58 g of crude moist 6-methyl-2-nitraminopyridine. This solid was carefully added in 1–2 g portions to stirred H₂SO₄ (70 mL) at 40° C. After complete addition, the reaction mixture was stirred 1 h at 40° C., cooled and poured into 500 g of ice. The resulting precipitate was filtered, washed with 50 mL of H₂O, and air dried to give a yellow solid.

8.5 g of this mixture of 2-amino-6-methyl-3-nitropyridine and 2-amino-6-methyl-5-nitropyridine was dissolved in H₂SO₄ (100 mL) at 0° C. and HNO₃ (2.74 mL, d=1.49) was added drop-wise over 10 min. After complete addition, the mixture was warmed to 50° C. for 90 min., cooled, then poured onto 200 g of ice. The residue was collected by filtration and washed with cold H₂O (2×50 mL) to give 2-amino-6-methyl-3,5-dinitropyridine as a yellow solid.

Step 2: Preparation of 2-butyl-5-methyl-6-[(1-oxopentyl)amino]imidazo[4,5-b]pyridine The title compound was prepared from 2-amino-6-methyl-3,5-dinitropyridine by the method described in Example 1, Step 2.

¹H NMR (CDCl₃, 400 MHz): d 7.79 (s, 1H), 2.88 (t, 2H, J=7.6 Hz), 2.50 (s, 3H), 2.45 (t, 2H, J=7.4 Hz), 1.85–1.66 (m, 4H), 1.50–1.34 (m, 4H), 0.97 (t, 3H, J=7.4 Hz), 0.95 (t, 3H, J=7.4 Hz).

Step 3: Preparation of 2-Butyl-3-[[2'-[[(1,1-dimethylethyl)amino]sulfonyl][1,1'-biphenyl]-4-yl]-methyl]-5-methyl-6-[(1-oxopentyl)amino]-3H-imidazo[4,5-b]pyridine The title compound was prepared from 2-butyl-5-methyl-6-[(1-oxopentyl)amino]imidazo[4,5-b]-pyridine by the method described in Example 1, Step 3.

Step 4: Preparation of 2-Butyl-3-[[2'-[[(amino)sulfonyl][1,1'-biphenyl]-4-yl]methyl]-5-methyl-6-[(1-oxopentyl)amino]-3H-imidazo[4,5-b]-pyridine The title compound was prepared from 2-Butyl-3-[[2'-[[(1,1-dimethylethyl)amino]sulfonyl]-[1,1'-biphenyl]-4-yl]methyl]-5-methyl-6-[(1-oxopentyl)-amino]-3H-imidazo[4,5-b]pyridine by the method described in Example 1, Step 4.

Step 5: Preparation of 2-butyl-3-[[2'-[[(1-oxopentyl)-amino]sulfonyl][1,1'-biphenyl]-4-yl]methyl]-5-methyl-6-[(1-oxopentyl)amino]-3H-imidazo[4,5-b]pyridine The title compound was prepared from 2-Butyl-3-[[2'-[[(amino)sulfonyl][1,1'-biphenyl]-4-yl]-methyl]-5-methyl-6-[(1-oxopentyl)amino]-3H-imidazo[4,5-b]pyridine and valeryl chloride as described in Example 1, Step 5.
MS (FAB): 619 (M+ +1).

EXAMPLE 6

2-Butyl-3-[[2'-[[(3-cyclopentyl-1-oxopropyl)amino]sulfonyl][1,1'-biphenyl]-4-yl]methyl]-5-methyl-6-[(1-oxopentyl)amino]-3H-imidazo[4,5-b]pyridine To a solution of 2-butyl-3-[2'-aminosulfonyl]-[1,1'-biphenyl]-4-yl]methyl]-5-metyl-6-[(1-oxopentyl)-amino]-3H-imidazo[4,5-b]pyridine (66 mg, 0.124 mmol) and DMAP (30 mg, 0.248 mmol) in pyridine (1 mL) was added 3-cyclopentylpropionyl chloride (200 mL, 1.31 mmol) at rt. After the solution was stirred at rt for 18 h, the reaction was quenched with MeOH. The solution was diluted with EtOAc, washed with brine, and dried over MgSO4. Concentration followed by flash chromatography (hexanes: EtOAc=1:1, 100% EtOAc, 10% MeOH/EtOAc) afforded 2-butyl-3-[[2'-[[(3-cyclopentyl-1-oxopropyl)amino]sulfonyl][1,1'-biphenyl]-4-yl]-methyl]-5-methyl-6-[(1-oxopentyl)amino]-3H-imidazo[4,5-b]pyridine as a solid.
MS (FAB): 658 (M+ +1).

EXAMPLE 7

2-butyl-3-[[2'-[[(3-phenyl-1-oxopropyl)amino]sulfonyl]-[1,1'-biphenyl]-4-yl]methyl]-5-methyl-6-](1-oxopentyl)-amino]-3H-imidazo[4,5-b]pyridine Step 1: Preparation of 2-butyl-3-[2'-aminosulfonyl]-[1,1'-biphenyl]-4-yl]methyl]-5-metyl-6-[(1-oxopentyl-)amino]-3H-imidazo[4,5-b]pyridine To a suspension of 60% NaH (168 mg, 4.21 mmol) in DMF (10 mL) was added a suspension of 2-butyl-5-methyl-6-[(1-oxopentyl)amino]imidazo[4,5-b]-pyridine (1.21 g, 4.21 mmol) in DMF (16 mL) in two portions at 0_C. The mixture was stirred at 0_C for 20 min until the gas evolution ceased. To the above brown solution was added 4'-bromomethylbiphenyl-2-tert-butylsulfonamide (1.93 g, 5.05 mmol) in DMF (10 mL) dropwise at 0_C. The solution was stirred at 0_C for 30 min and at rt for 18 hrs. After DMF was evaporated in vacuo, the residue was partitioned between EtOAc and water. The aqueous layer was extracted with EtOAc (2X), washed with brine, and dried over anhydrous MgSO4. Concentration followed by flash chromatography (hexanes :EtOAc=1:1, 100% EtOAc, 10% MeOH-/EtOAc) afforded 1.36 g of foamy solid. The above solid was dissolved in anhydrous TFA and was stirred at rt for 18 h. After TFA was removed in vacuo, the residue was dissolved in EtOAc and washed with saturated aq. NaHCO3. The aqueous layer was extracted with EtOAc (2X). The combined organic layer was washed with brine, and dried over anhydrous MgSO4. Concentration afforded the title compound as a foamy powder.

Step 2: Preparation of 2-butyl-3-[[2'-[[(3-phenyl-1-oxopropyl)amino]sulfonyl][1,1'-biphenyl]-4-yl]methyl]-5-methyl-6-[(1-oxopentyl)amino]-3H-imidazo[4,5-b]pyridine A THF (15 mL) solution of hydrocinnamic acid (751 mg, 5 mmol) and carbonyl-di-imidazole (811 mg, 5 mmol) was refruxed for 3 h. To the above solution was added a THF (10 mL) solution of DBU (448 mL, 3 mmol) and 2-butyl-3-[2'-aminosulfonyl][1,1'-biphenyl]-4-yl]-methyl]-5-methyl-6-[(1-oxopentyl)amino]-3H-imidazo[4,5-b]pyridine (533 mg, 1 mmol). The refluxing was continued for 18 h. After cooling, the solution was diluted with EtOAc, washed with 20% aq. citric acid and brine, and dried over MgSO4. Concentration followed by flash chromatography (hexanes: EtOAc=1:1, 100% EtOAc, 10% MeOH/EtOAc) afforded 2-butyl-3-[[2'-[[(3-phenyl-1-oxopropyl)amino]sulfonyl]-[1,1'-biphenyl]-4-yl]methyl]-5-methyl-6-[(1-oxopentyl)-amino]-3H-imidazo[4,5-b]pyridine as a solid.
MS (FAB): 666 (M+ +1)

EXAMPLE 8

2-butyl-3-[[2'-[[[(butylamino)carbonyl]amino]sulfonyl]-[1,1'-biphenyl]-4-yl]methyl]-5-methyl-6-[(1-oxopentyl)-amino]-3H-imidazo[4,5-b]pyridine To a solution of 2-butyl-3-[2'-aminosulfonyl]-[1,1'-biphenyl]-4-yl]methyl]-5-metyl-6-[(1-oxopentyl)-amino]-3H-imidazo[4,5-b]pyridine (117 mg, 0.22 mmol) and DBU (100.5 mg, 0.66 mmol) in THF (3 mL) was added butylisocyanate (43.6 mg, 0.44 mmol) at rt. After the solution was stirred at rt for 2 h, the reaction was quenched with MeOH. The solution was diluted with EtOAc, washed with 20% aqueous citric acid and brine, and dried over anhydrous MgSO4. Concentration followed by flash chromatography (100% EtOAc, 10% MeOH/EtOAc, 10% MeOH/CH2Cl2) afforded the title compound as a solid.
MS (FAB): 633 (M+ +1)

EXAMPLE 9

2-butyl-3-[[2'-[[[(butylamino)carbonyl]amino]sulfonyl]-[1,1'-biphenyl]-4-yl]methyl]-5-methyl-6-[[(2-propylamino)carbonyl]amino]-3H-imidazo[4,5-b]pyridine Step 1: Preparation 2-butyl-3-[2'-aminosulfonyl][1,1'-biphenyl]-4-yl]methyl]-5-methyl-6-[[(2-propylamino)-carbonyl]amino]-3H-imidazo[4.5-b]pyridine To a solution of 2-butyl-3-[2'-(1,1-dimethylethyl-)aminosulfonyl][1,1'-biphenyl]-4-yl]methyl]-5-methyl-6-[(1-oxopentyl)amino]-3H-imidazo[4,5-b]pyridine (347 mg, 0.589 mmol) in MeOH (3 mL) was added conc. HCl (2 mL). After the solution was stirred at rt for 42 h, the solution was diluted with EtOAc, neutralized by saturated aq. NaHCO3, washed with brine, and dried over anhydrous MgSO4. Concentration followed by flash chromatography (100% EtOAc, 10% MeOH/EtOAc) afforded 2-butyl-3-[2'-(1,1-dimethylethyl)aminosulfonyl][1,1'-biphenyl]4-yl]methyl]-5-methyl-6-amino-3H-imidazo[4,5-b] pyridine as a solid. To this solid (100 mg, 0.198 mmol) and DMAP (10 mg, 0.08 mmol) in pyridine (2 mL) was added iso-propylisocyanate (24 mL, 0.24 mmol). After the solution was stirred at rt for 18 h, the solution was quenched with MeOH, and stirred at rt for additional 2 h. Concentration gave a brown glass, which was dissolved in TFA (2 mL) and stirred at rt for 18 h. After TFA was removed in vacuo, the residue was dissolved in EtOAc and washed with saturated aq. NaHCO$_3$. The aqueous layer was extracted with EtOAc (2X). The combined organic layer was washed with brine, and dried over anhydrous MgSO$_4$. Concentration followed by flash chromatography (hexanes: EtOAc=1:1, 100% EtOAc, 10% MeOH-/EtOAc) afforded the title compound as a foamy powder.

Step 2: Preparation of 2-butyl-3-[[2'-[[[(butylamino)-carbonyl]amino]sulfonyl][1,1'-biphenyl]-4-yl]-methyl]-5-methyl-6-[[(2-propylamino)carbonyl]-amino]-3H-imidazo[4,5-b]pyridine The title compound was prepared from 2-butyl-3-[2'-aminosulfonyl][1,1'-biphenyl]-4-yl]methyl]-5-methyl-6-[[(2-propylamino)carbonyl]amino]-3H-imidazo-[4,5-b]pyridine and butyl-isocyanate according to the method described in Example 8.

MS (FAB): 634 (M$^+$+1)

Example 10

5,7-dimethyl-2-propyl-3-[[2'-[[(3-cyclopentyl-1-oxo-propyl)amino]sulfonyl][1,1'-biphenyl]-4-yl]methyl]-6-[(1-oxobutyl)amino]-3H-imidazo[4,5-b]pyridine Step 1: Preparation of 2-amino-6-methyl-3,5-dinitropyridine The title compound is prepared using the method outlined in Example 5 step 1 starting with 2-amino-4,6-dimethypyridine in the place of 2-amino-6-methylpyridine.

Step 2: Preparation of 5,7-dimethyl-2-propyl-6-[(1-oxobutyl)amino]imidazo[4,5-b]pyridine The title compound is prepared using the method outlined in Example 5 step 2 starting with 2-amino-4,6-dimethyl-3,5-dinitropyridine in the place of 2-amino-6-methylpyridine and butyric acid in the place of valeric acid.

Step 3: Preparation of 5,7-dimethyl-2-propyl-3-[[2'-(aminosulfonyl)[1,1'-biphenyl]-4-yl]methyl]-6-[(1-oxobutyl)amino]-3H-imidazo[4,5-b]pyridine The title compound was prepared from 2-propyl-5,7-dimethyl-6-[(1-oxobutyl)amino]imidazo[4,5-b]pyridine by the method described in Example 5, Steps 3 and 4.

Step 4: Preparation of 5,7-dimethyl-2-propyl-3-[[2'-[[(3-cyclopentyl-1-oxopropyl)amino]-sulfonyl][1,1'-biphenyl]-4-yl]methyl]-6-[(1-oxobutyl)amino]-3H-imidazo[4,5-b]pyridine The title compound was prepared from 5,7-dimethyl-2-propyl-3-[[2'-(aminosulfonyl)[1,1-biphenyl]-4-yl]methyl]-6-[(1-oxobutyl)amino]-3H-imidazo-[4,5-b]pyridine by the method described in Example 1, Step 5.

FAB MS 644 (M$^+$+1).

EXAMPLE 11

7-methyl-2-propyl-3-[[2'-[[[(butylamino)carbonyl]amino]-sulfonyl][1,1'-biphenyl]-4-yl]methyl]-6-[(1-oxobutyl)-amino]-3H-imidazo[4,5-b]pyridine Step 1: Preparation of 7-methyl-2-propyl-6-[(1-oxobutyl)amino]3H-imidazo[4,5-b]pyridine The title compound was prepared from 2-amino-4-methyl-3,5-dinitropyridine according to method described in Example 1, Step 2 using butyric acid in the place of valeric acid.

Step 2: Preparation of 7-methyl-2-propyl-3-[[2'-(aminosulfonyl)[1,1'-biphenyl]-4-yl]methyl]-6-[(1-oxobutyl)amino]-3H-imidazo[4,5-b]pyridine The title compound was prepared from 7-methyl-2-propyl-6-[(1-oxobutyl)amino]-3H-imidazo[4,5-b]pyridine according to method described in Example 1, Step 3.

Step 3: Preparation of 7-methyl-2-propyl-3-[[2'-[[[(butylamino)carbonyl]amino]sulfonyl][1,1'-biphenyl]-4-yl]methyl]-6-[(1-oxobutyl)amino]-3H-imidazo[4,5-b]pyridine The title compound was prepared from 7-methyl-2-propyl-3-[[2'-(aminosulfonyl)[1,1'-biphenyl]-4-yl]methyl]-6-[(1-oxobutyl)amino]-3H-imidazo[4,5-b]pyridine by the method described in Example 3.

FAB MS 643 (M$^+$+39); C$_{32}$H$_{40}$N$_6$SO$_4$+K.

EXAMPLE 12

2-butyl-3-[[2'-[[(benzoyl)amino]sulfonyl][1,1'-biphenyl]-4-yl]methyl]-5-methyl-6-[(1-oxopentyl)amino]-3H-imidazo[4,5-b]pyridine The title compound was prepared from 2-Butyl-3-[[2'-[[(amino)sulfonyl][1,1'-biphenyl]-4-yl]methyl]-5-methyl-6-[(1-oxopentyl)amino]-3H-imidazo[4,5-b]pyridine and benzoyl chloride as described in Example 1, Step 5.

MS (FAB): 642 (M$^+$+1)

EXAMPLE 13

Preparation of 4'-bromomethylbiphenyl-2-tert-butylsulfonamide

Step 1: Preparation of 2-bromobenzene(tert-butyl)-sulfonamide

To a stirred solution of 2-bromobenzenesulfonyl chloride (Lancaster Synthesis) (2.21 g, 8.65 mmol) in chloroform (40 ml) under nitrogen at room temperature was added tert-butylamine (Aldrich) (2.30 ml, 21.9 mmol). The orange solution was stirred at room temperature for 12 h, then the mixture evaporated to dryness. Flash chromatography (silica gel, 10,15% ethyl acetate-hexane) afforded 2-bromobenzene(tert-butyl)sulfonamide as a white solid; $^1$H NMR (300 MHz, CDCl$_3$) δ 8.18 (d, J=8.5 Hz, 1H), 7.73 (d, J=8.5 Hz, 1H), 7.50–7.35 (m, 2H), 5.11 (s, 1H), 1.20 (s, 9H).

Step 2: Preparation of p-tolyltrimethyltin p-Tolylmagnesium bromide solution (Aldrich) (1.0M solution in diethyl ether) (53 ml, 0.0530 mol) was added dropwise to trimethyltin chloride (6.92 g, 0.0347 mol) in tetrahydrofuran (50 ml) under nitrogen at −10° C. The suspension was allowed to warm slowly to room temperature over 3 h then saturated ammonium chloride solution (10 ml) was added followed by sufficient water to dissolve the precipitate. The solution was extracted three times with diethyl ether-hexane (1:1). The combined organic phase was washed with brine, dried (magnesium sulfate) and the solvents removed in vacuo. Vacuum distillation of the residue afforded a colorless liquid (39°–40° C., 0.1 mm Hg) which was further purified by flash chromatography (silica gel, hexane) to give p-tolyltrimethyltin as a colorless liquid; $^1$H NMR (300 MHz, CDCl$_3$) δ 7.40 (d, J =7.7 Hz, 2H), 7.19 (d, J=7.7 Hz, 2H), 2.34 (s, 3H), 0.30 (s, 9H).

Step 3: Preparation of 4'-methylbiphenyl-2-tert-butyl sulfonamide

2-Bromobenzene(tert-butyl)sulfonamide (1.00 g, 3.92 mmol), p-tolyl-trimethyltin (1.95 g, 6.67 mmol), bis(triphenylphosphine)palladium(II) chloride (Aldrich) (165 mg, 0.235 mmol) and dimethylformamide (25 ml) were heated with stirring under nitrogen at 90° C. for 5 h. The black suspension was cooled to room temperature, then filtered through a pad of celite which was washed with tetrahydrofuran. The colorless filtrate was evaporated to dryness then chromatographed (silica gel, 8,10% ethyl acetate-hexane) to give 4'-methylbiphenyl-2-tert-butylsulfonamide as a white solid; $^1$H NMR (300 MHz, CDCl$_3$) δ 8.16 (d, J =7.9 Hz, 1H), 7.60–7.37 (m, 4H), 7.36–7.24 (m, 3H), 3.57 (s, 1H), 2.42 (s, 3H), 0.99 (s, 9H).

Step 4: Preparation of 4'-bromomethylbiphenyl-2-tert-butylsulfonamide

N-Bromosuccinimide (0.387 g, 2.17 mmol), a,a'-azoisobutyronitrile (catalytic), 4'-methylbiphenyl-2-tert-butylsulfonamide (0.55 g, 1.81 mmol) and carbon tetrachloride (50 ml) were heated with stirring at reflux for 3 h. After cooling to room temperature the mixture was filtered and the filtrate evaporated to dryness. Flash chromatography (silica gel, 10,20% ethyl acetate-hexane) afforded 4'-bromomethylbiphenyl-2-tert-butylsulfonamide (77% pure (the remainder of the material was 4'-dibromomethylbiphenyl-2-tert-butylsulfonamide)) as a white solid; $^1$H NMR (300 MHz, CDCl$_3$) δ 8.17 (dd, J=7.5, 1.6 Hz, 1H), 7.68–7.45 (m, 6H), 7.31 (dd, J=7.5, 1.6 Hz, 1H), 4.55 (s, 2H), 3.52 (s, 1H), 1.00 (s, 9H).

EXAMPLES 14–16

2-butyl-3-[[2'-[[(3-cyclopentyl-1-oxopropyl)amino]-sulfonyl][1,1'-biphenyl]-4-yl]methyl]-6-[(1-oxopentyl)-amino]-7-methyl-3H-imidazo[4,5-b]pyridine 2-butyl-3-[[2'-[[(3,5-bis-trifluoromethylbenzoyl)-amino]sulfonyl][1,1'-biphenyl]-4-yl]methyl]-6-[(1-oxobutyl)amino]-7-mehtyl-3H-imidazo[4,5-b]pyridine 2-propyl-3-[[(4-propylbenzoyl)amino]sulfonyl][1,1'-biphenyl]-4-yl]methyl]-6-[(1-oxobutyl)amino]-7-methyl-3H-imidazo[4,5-b]pyridine The above identified compounds were prepared according to the procedures outlined in Example 4, Steps 1 to 5 and Example 11, Step 1.

EXAMPLES 17–19

2-butyl-3-[[2'-[[(1-oxopentyl)amino]sulfonyl][1,1'-biphenyl]-4-yl]methyl]-6-[(1-oxopentyl)amino]-3H-imidazo[4,5-b]pyridine 2-butyl-3-[[2'-[[(3,5-bis-trifluoromethylbenzoyl)amino]-sulfonyl][1,1'-biphenyl]-4-yl]methyl]-6-[(1-oxopentyl)-amino]-3H-imidazo[4,5-b]pyridine 2-butyl-3-[[2'-[[(4-propylbenzoyl)amino]sulfonyl][1,1'-biphenyl]-4-yl]methyl]-6-[(1-oxopentyl)amino]-3H-imidazo[4,5-b]pyridine The above identified compounds were prepared according to the procedures outlined in Example 1.

What is claimed is:

1. A compound of structural formula I

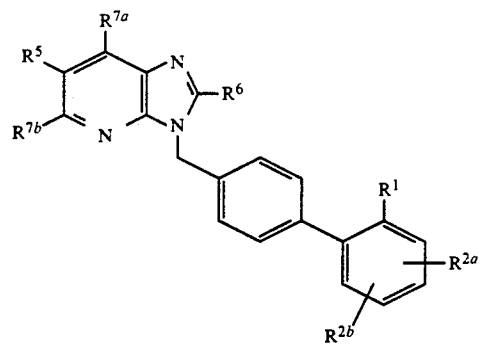

or a pharmaceutically acceptable salt thereof wherein:
$R^1$ is:
- (a) —SO$_2$NHC(O)R$^{23}$,
- (b) —SO$_2$NHC(O)NR$^4$R$^{23}$, or
- (c) —SO$_2$NHC(O)N[CH$_2$CH$_2$]$_2$O;

$R^{2a}$ and $R^{2b}$ are independently:
- (a) H,
- (b) Cl, Br, I, F,
- (c) C$_1$–C$_6$-alkyl, unsubstituted or substituted with aryl, furyl, thienyl, pyridyl, C$_3$–C$_6$-cycloalkyl, F, C$_1$–C$_6$-alkoxy, polyfluoro-C$_1$–C$_4$-alkyl, morpholine, pyrrolidine, and —N(R$^4$)(R$^{23}$),
- (d) C$_1$–C$_6$-alkoxy, unsubstituted or substituted with F and polyfluoro-C$_1$–C$_4$-alkyl,
- (e) C$_1$–C$_6$-alkoxyalkyl, or
- (f) aryl;

wherein aryl is phenyl or naphthyl substituted or unsubstituted with one or two substituents selected from the group consisting of Cl, Br, I, F, C$_1$–C$_4$-alkyl, C$_1$–C$_4$-alkoxy, CF$_3$, C$_1$–C$_4$-alkylthio, OH, NH(C$_1$–C$_4$-alkyl), N(C$_1$–C$_4$-alkyl)$_2$, CO$_2$H, and CO$_2$-C$_1$–C$_4$-alkyl;

$R^4$ is:
- (a) H,
- (b) aryl, wherein aryl is as defined above, or
- (c) C$_1$–C$_6$-alkyl, substituted or unsubstituted with aryl, furyl, thienyl, pyridyl, C$_3$–C$_6$-cycloalkyl, and F;

R4a is:
- (a) H,
- (b) aryl, wherein aryl is as defined above, or
- (c) C$_1$–C$_6$-alkyl, substituted or unsubstituted with aryl, furyl, thienyl, pyridyl, C$_3$–C$_6$-cycloalkyl, and F;

$R^5$ is:
- (a) —NH$_2$,
- (b) —N(R$^4$)R$^{23}$,
- (c) —N(R$^4$)COR$^{23}$,
- (d) —N(R$^4$)(C$_3$–C$_7$-cycloalkyl),
- (e)

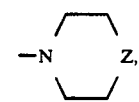

- (f) —NHSO$_2$CF$_3$,
- (g) —NHSO$_2$R$^{23}$,
- (h) —NHSO$_2$NHR$^{23}$,
- (i) —NHSO$_2$NHCOR$^{23}$,
- (j) —NHSO$_2$NHSO$_2$R$^{23}$,
- (k) —N(R$^4$)CO$_2$R$^{23}$,
- (l) —N(R$^4$)CON(R$^4$)(R$^{23}$), (m)

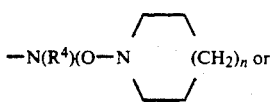

(n)

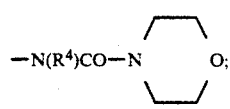

n is: 0, 1 or 2;
Z is:
(a) (CH₂)n,
(b) NR⁴,
(c) NCOR²³,
(d) NCO₂R²³,
(e) NSO₂R²³, or
(f) O;

R⁶ is:
(a) $C_1-C_9$-alkyl, $C_2-C_6$-alkenyl or $C_2-C_6$-alkynyl, which is substituted or unsubstituted with a substituent selected from the group consisting of: aryl as defined above, $C_3-C_7$-cycloalkyl, Cl, Br, I, F, -CF₂CF₃, -N($C_1-C_4$-alkyl)₂, —CF₃, —CF₂CH₃, $C_1-C_4$-alkoxy; or
(b) polyfluoro-$C_1-C_4$-alkyl,
(c) $C_3-C_7$-cycloalkyl, unsubstituted or substituted with one or two substituents selected from the group consisting of: $C_1-C_4$-alkyl or —CF₃ or
(d) $C_1-C_6$-alkyloxy;

R⁷ᵃ and R⁷ᵇ are independently:
(a) H,
(b) —$C_1-C_5$-alkyl,
(c) —$C_1-C_5$-polyfluoroalkyl,
(d) —$C_3-C_6$-cycloalkyl,
(e) Cl, Br, I, F,
(f) —O—$C_1-C_5$-alkyl,
(g) —S—$C_1-C_5$-alkyl,
(h) —CO₂R⁴, or
(i) —CON(R⁴)(R²³);

R²³ is:
(a) aryl as defined above,
(b) heteroaryl as defined below,
(c) $C_3-C_6$-cycloalkyl,
(d) $C_1-C_7$-alkyl which can be optionally substituted with a substituent that is a member selected from the group consisting of aryl as defined above, heteroaryl as defined below, —$C_3-C_7$-cycloalkyl, —O($C_3-C_7$-cycloalkyl) —OH, SH, —$C_1-C_4$-alkyl, —O($C_1-C_4$-alkyl), —S($C_1-C_4$-alkyl), —CF₃, Cl, Br, F, I, —CO₂H, —CO₂—$C_1-C_4$-alkyl, —NH₂, —NH($C_1-C_4$-alkyl), —NHCOR⁴ᵃ, —N($C_1-C_4$-alkyl)₂, and —OC₆H₅, or
(e) polyfluoro-$C_1-C_4$-alkyl; and wherein heteroaryl is defined as a 5- or 6-membered aromatic ring containing 1, 2 or 3 heteroatoms selected from the group consisting of O, N, and S.

2. The compound of claim 1 of structural Formula II

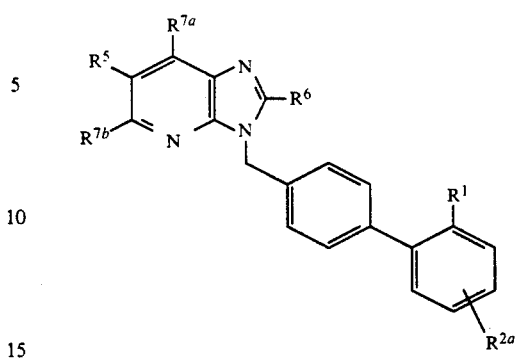

or a pharmaceutically acceptable salt thereof wherein:
R¹ is:
(a) SO₂NHCOR²³, or
(b) SO₂NHCONR⁴R²³;

R²ᵃ is:
(a) H,
(b) $C_1-C_6$-alkyl or $C_1-C_6$-alkoxy, unsubstituted or substituted with polyfluoro-$C_1-C_4$-alkyl;

R⁵ is:
(a) —N(R⁴)COR²³,
(b) —NHSO₂R²³,
(c) —N(R⁴)CO₂R²³,
(d) —N(R⁴)CON(R⁴)R²³,
(e)

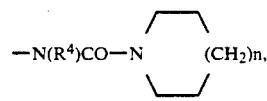

(f)

(g)

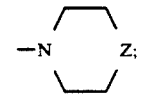

n is 0, 1, or 2;
Z is:
(a) O,
(b) NCOR²³,
(c) NCO₂R²³,
(d) NSO₂R²³, or
(e) (CH₂)n; and R⁷ᵃ and R⁷ᵇ are independently:
(a) H,
(b) $C_1-C_5$-alkyl, or
(c) CO₂R⁴.

3. The compound of claim 2 of structural formula:

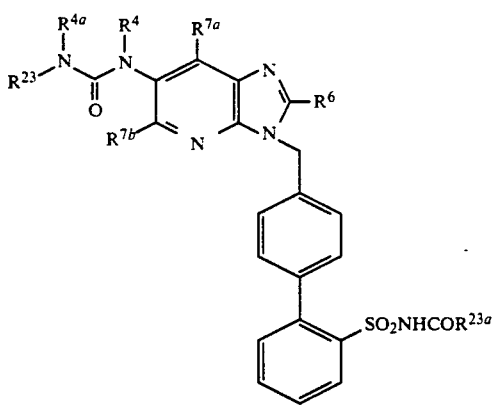

wherein:

$R^{7a}$ and $R^{7b}$ are independently: H or $CH_3$ and all other substituents are as defined Table A below, wherein $C_5H_9$ represents cyclopentyl.

TABLE A

| $R^6$ | $NR^{4a}R^{23}$ | $R^4$ | $R^{23a}$ |
|---|---|---|---|
| $(CH_2)_3CH_3$ | NHEt | H | $(CH_2)_2CH_3$ |
| $(CH_2)_3CH_3$ | NHEt | Me | $(CH_2)_3CH_3$ |
| $(CH_2)_3CH_3$ | NHEt | H | $CH_2CH_2(C_5H_9)$ |
| $(CH_2)_3CH_3$ | NEEt | H | $CH_2CH_2(C_6H_5)$ |
| $(CH_2)_3CH_3$ | NHEt | Me | $CH_2CH_2(C_6H_5)$ |
| $(CH_2)_3CH_3$ | NHEt | H | $CH_2CH_2OCH(CH_3)_2$ |
| $(CH_2)_3CH_3$ | NHEt | H | $CH_2O(C_6H_5)$ |
| $(CH_2)_3CH_3$ | NHEt | H | $CH_2CH_2$-thiophene-2-yl |
| $(CH_2)_3CH_3$ | NHEt | H | $C_6H_5$ |
| $(CH_2)_3CH_3$ | NHEt | H | 3,5-dimethylphenyl-1-yl |
| $(CH_2)_3CH_3$ | NHEt | H | 3,5-bis(trifluoromethyl)-phenyl-1-yl |
| $(CH_2)_2CH_3$ | NHEt | H | $(CH_2)_2CH_3$ |
| $(CH_2)_2CH_3$ | NHEt | Me | $(CH_2)_3CH_3$ |
| $(CH_2)_2CH_3$ | NHEt | H | $CH_2CH_2(C_5H_9)$ |
| $(CH_2)_2CH_3$ | NHEt | H | $CH_2CH_2(C_6H_5)$ |
| $(CH_2)_2CH_3$ | NHEt | Me | $CH_2CH_2(C_6H_5)$ |
| $(CH_2)_2CH_3$ | NHEt | H | $CH_2CH_2OCH(CH_3)_2$ |
| $(CH_2)_2CH_3$ | NHEt | H | $CH_2O(C_6H_5)$ |
| $(CH_2)_2CH_3$ | NHEt | H | $CH_2CH_2$-thiophene-2-yl |
| $(CH_2)_2CH_3$ | NHEt | H | $C_6H_5$ |
| $(CH_2)_2CH_3$ | NHEt | H | 3,5-dimethylphenyl-1-yl |
| $(CH_2)_2CH_3$ | NHEt | H | 3,5-bis(trifluoromethyl)-phenyl-1-yl |
| $(CH_2)_3CH_3$ | NHPr | H | $(CH_2)_2CH_3$ |
| $(CH_2)_3CH_3$ | NHPr | Me | $(CH_2)_3CH_3$ |
| $(CH_2)_3CH_3$ | NHPr | H | $CH_2CH_2(C_5H_9)$ |
| $(CH_2)_3CH_3$ | NHPr | H | $CH_2CH_2(C_6H_5)$ |
| $(CH_2)_3CH_3$ | NHPr | Me | $CH_2CH_2(C_6H_5)$ |
| $(CH_2)_3CH_3$ | NHPr | H | $CH_2CH_2OCH(CH_3)_2$ |
| $(CH_2)_3CH_3$ | NHPr | H | $CH_2O(C_6H_5)$ |
| $(CH_2)_3CH_3$ | NHPr | H | $CH_2CH_2$-thiophene-2-yl |
| $(CH_2)_3CH_3$ | NHPr | H | $C_6H_5$ |
| $(CH_2)_3CH_3$ | NHPr | H | 3,5-dimethylphenyl-1-yl |
| $(CH_2)_3CH_3$ | NHPr | H | 3,5-bis(trifluoromethyl)-phenyl-1-yl |
| $(CH_2)_2CH_3$ | NHPr | H | $(CH_2)_2CH_3$ |
| $(CH_2)_2CH_3$ | NHPr | Me | $(CH_2)_3CH_3$ |
| $(CH_2)_2CH_3$ | NHPr | H | $(CH_2CH_2(C_5H_9)$ |
| $(CH_2)_2CH_3$ | NHPr | H | $CH_2CH_2(C_6H_5)$ |
| $(CH_2)_2CH_3$ | NHPr | Me | $CH_2CH_2(C_6H_5)$ |
| $(CH_2)_2CH_3$ | NHPr | H | $CH_2CH_2OCH(CH_3)_2$ |
| $(CH_2)_2CH_3$ | NHPr | H | $CH_2O(C_6H_5)$ |
| $(CH_2)_2CH_3$ | NHPr | H | $CH_2CH_2$-thiophene-2-yl |
| $(CH_2)_2CH_3$ | NHPr | H | $C_6H_5$ |
| $(CH_2)_2CH_3$ | NHPr | H | 3,5-dimethylphenyl-1-yl |
| $(CH_2)_2CH_3$ | NHPr | H | 3,5-bis(trifluoromethyl)-phenyl-1-yl |
| $(CH_2)_3CH_3$ | $N(CH_3)Pr$ | H | $(CH_2)_2CH_3$ |
| $(CH_2)_3CH_3$ | $N(CH_3)Pr$ | Me | $(CH_2)_3CH_3$ |
| $(CH_2)_3CH_3$ | $N(CH_3)Pr$ | H | $CH_2CH_2(C_5H_9)$ |
| $(CH_2)_3CH_3$ | $N(CH_3)Pr$ | H | $CH_2CH_2(C_6H_5)$ |
| $(CH_2)_3CH_3$ | $N(CH_3)Pr$ | Me | $CH_2CH_2(C_6H_5)$ |
| $(CH_2)_3CH_3$ | $N(CH_3)Pr$ | H | $CH_2CH_2OCH(CH_3)_2$ |
| $(CH_2)_3CH_3$ | $N(CH_3)Pr$ | H | $CH_2O(C_6H_5)$ |
| $(CH_2)_3CH_3$ | $N(CH_3)Pr$ | H | $CH_2CH_2$-thiophene-2-yl |
| $(CH_2)_3CH_3$ | $N(CH_3)Pr$ | H | $C_6H_5$ |
| $(CH_2)_3CH_3$ | $N(CH_3)Pr$ | H | 3,5-dimethylphenyl-1-yl |

TABLE A-continued

| R⁶ | NR⁴ᵃR²³ | R⁴ | R²³ᵃ |
|---|---|---|---|
| (CH₂)₃CH₃ | N(CH₃)Pr | H | 3,5-bis(trifluoromethyl)-phenyl-1-yl |
| (CH₂)₂CH₃ | N(CH₃)Pr | H | (CH₂)₂CH₃ |
| (CH₂)₂CH₃ | N(CH₃)Pr | Me | (CH₂)₃CH₃ |
| (CH₂)₂CH₃ | N(CH₃)Pr | H | CH₂CH₂(C₅H₉) |
| (CH₂)₂CH₃ | N(CH₃)Pr | H | CH₂CH₂(C₆H₅) |
| (CH₂)₂CH₃ | N(CH₃)Pr | Me | CH₂CH₂(C₆H₅) |
| (CH₂)₂CH₃ | N(CH₃)Pr | H | CH₂CH₂OCH(CH₃)₂ |
| (CH₂)₂CH₃ | N(CH₃)Pr | H | CH₂O(C₆H₅) |
| (CH₂)₂CH₃ | N(CH₃)Pr | H | CH₂CH₂-thiophene-2-yl |
| (CH₂)₂CH₃ | N(CH₃)Pr | H | C₆H₅ |
| (CH₂)₂CH₃ | N(CH₃)Pr | H | 3,5-dimethylphenyl-1-yl |
| (CH₂)₂CH₃ | N(CH₃)Pr | H | 3,5-bis(trifluoromethyl)-phenyl-1-yl |
| (CH₂)₃CH₃ | NH-iso-Pr | H | (CH₂)₃CH₃ |
| (CH₂)₃CH₃ | NH-iso-Pr | H | CH₂CH₂(C₆H₅) |
| (CH₂)₂CH₃ | NH-iso-Pr | Me | (CH₂)₃CH₃ |
| (CH₂)₂CH₃ | NH-iso-Pr | H | CH₂CH₂(C₆H₅) |
| (CH₂)₃CH₃ | NH-iso-Pr | H | CH₂CH₂CH(CH₃)₂ |
| (CH₂)₃CH₃ | N(CH₃)-iso-Pr | H | (CH₂)₃CH₃ |
| (CH₂)₃CH₃ | N(CH₃)-iso-Pr | H | CH₂CH₂(C₆H₅) |
| (CH₂)₂CH₃ | N(CH₃)-iso-Pr | Me | (CH₂)₃CH₃ |
| (CH₂)₂CH₃ | N(CH₃)-iso-Pr | H | CH₂CH₂(C₆H₅) |
| (CH₂)₂CH₃ | N(CH₃)-iso-Pr | H | CH₂CH₂CH(CH₃)₂ |
| (CH₂)₂CH₃ | NH-iso-Pr | H | CH₂CH₂CH(CH₃)₂. |

4. The compound of claim 2 of structural formula:

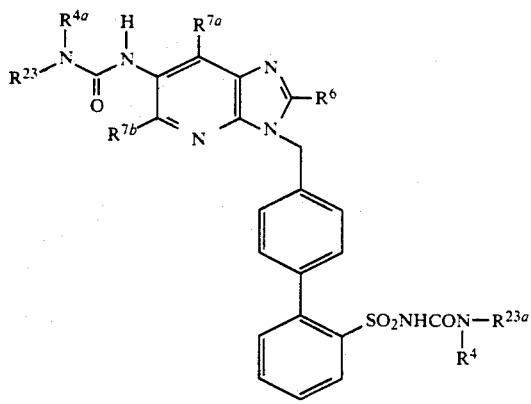

wherein:

$R^{7a}$ and $R^{7b}$ are independently: H or CH₃, and all other substituents are as defined in Table B below:

TABLE B

| R⁶ | NR⁴ᵃR²³ | NR⁴R²³ᵃ |
|---|---|---|
| (CH₂)₃CH₃ | NHEt | NH(CH₂)₃CH₃ |
| (CH₂)₃CH₃ | NHEt | NHCH₂CH(CH₃)₂ |
| (CH₂)₃CH₃ | NHEt | NH(CH₂)₂CH(CH₃)₂ |
| (CH₂)₃CH₃ | NHEt | NHCH₂(C₆H₅) |
| (CH₂)₃CH₃ | NHEt | N(CH₃)CH₂(C₆H₅) |
| (CH₂)₂CH₃ | NHEt | NH(CH₂)₃CH₃ |
| (CH₂)₂CH₃ | NHEt | NHCH₂CH(CH₃)₂ |
| (CH₂)₂CH₃ | NHEt | NH(CH₂)₂CH(CH₃)₂ |
| (CH₂)₂CH₃ | NHEt | NHCH₂(C₆H₅) |
| (CH₂)₂CH₃ | NHEt | N(CH₃)CH₂(C₆H₅) |
| (CH₂)₃CH₃ | NHPr | NH(CH₂)₃CH₃ |
| (CH₂)₃CH₃ | NHPr | NHCH₂CH(CH₃)₂ |
| (CH₂)₃CH₃ | NHPr | NH(CH₂)₂CH(CH₃)₂ |
| (CH₂)₃CH₃ | NHPr | NHCH₂(C₆H₅) |
| (CH₂)₃CH₃ | NHPr | N(CH₃)CH₂(C₆H₅) |
| (CH₂)₂CH₃ | NHPr | NH(CH₂)₃CH₃ |
| (CH₂)₂CH₃ | NHPr | NHCH₂CH(CH₃)₂ |
| (CH₂)₂CH₃ | NHPr | NH(CH₂)₂CH(CH₃)₂ |
| (CH₂)₂CH₃ | NHPr | NHCH₂(C₆H₅) |
| (CH₂)₂CH₃ | NHPr | N(CH₃)CH₂(C₆H₅) |
| (CH₂)₃CH₃ | NH-iso-Pr | NH(CH₂)₃CH₃ |
| (CH₂)₃CH₃ | NH-iso-Pr | NHCH₂CH(CH₃)₂ |
| (CH₂)₃CH₃ | NH-iso-Pr | NH(CH₂)₂CH(CH₃)₂ |
| (CH₂)₃CH₃ | NH-iso-Pr | NHCH₂(C₆H₅) |
| (CH₂)₃CH₃ | NH-iso-Pr | N(CH₃)CH₂(C₆H₅) |
| (CH₂)₂CH₃ | NH-iso-Pr | NH(CH₂)₃CH₃ |
| (CH₂)₂CH₃ | NH-iso-Pr | NHCH₂CH(CH₃)₂ |

TABLE B-continued

| $R^6$ | $NR^{4a}R^{23}$ | $NR^4R^{23a}$ |
|---|---|---|
| $(CH_2)_2CH_3$ | NH-iso-Pr | $NH(CH_2)_2CH(CH_3)_2$ |
| $(CH_2)_2CH_3$ | NH-iso-Pr | $NHCH_2(C_6H_5)$ |
| $(CH_2)_2CH_3$ | NH-iso-Pr | $N(CH_3)CH_2(C_6H_5)$ |
| $(CH_2)_3CH_3$ | $N(CH_3)$-iso-Pr | $NH(CH_2)_3CH_3$ |
| $(CH_2)_3CH_3$ | $N(CH_3)$-iso-Pr | $NHCH_2CH(CH_3)_2$ |
| $(CH_2)_3CH_3$ | $N(CH_3)$-iso-Pr | $NH(CH_2)_2CH(CH_3)_2$ |
| $(CH_2)_3CH_3$ | $N(CH_3)$-iso-Pr | $NHCH_2(C_6H_5)$ |
| $(CH_2)_3CH_3$ | $N(CH_3)$-iso-Pr | $N(CH_3)CH_2(C_6H_5)$ |
| $(CH_2)_2CH_3$ | $N(CH_3)$-iso-Pr | $NH(CH_2)_3CH_3$ |
| $(CH_2)_2CH_3$ | $N(CH_3)$-iso-Pr | $NHCH_2CH(CH_3)_2$ |
| $(CH_2)_2CH_3$ | $N(CH_3)$-iso-Pr | $NH(CH_2)_2CH(CH_3)_2$ |
| $(CH_2)_2CH_3$ | $N(CH_3)$-iso-Pr | $NHCH_2(C_6H_5)$ |
| $(CH_2)_2CH_3$ | $N(CH_3)$-iso-Pr | $N(CH_3)CH_2(C_6H_5)$. |

5. The compound of claim 2 of structural formula:

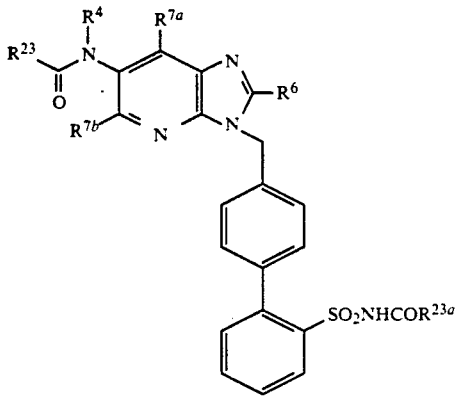

wherein:

$R^{7a}$ and $R^{7b}$ are independently: H or $CH_3$, and all other substitutents are as defined in Table C below, wherein $C_5H_9$ and $C_6H_{11}$ represent cylcopentyl and cyclohexyl, respectively:

TABLE C

| $R^6$ | $R^{23}$ | $R^4$ | $R^{23a}$ |
|---|---|---|---|
| $(CH_2)_3CH_3$ | $(CH_2)_3CH_3$ | H | $(CH_2)_2CH_3$ |
| $(CH_2)_3CH_3$ | $(CH_2)_3CH_3$ | H | $(CH_2)_3CH_3$ |
| $(CH_2)_3CH_3$ | $(CH_2)_3CH_3$ | Me | $(CH_2)_3CH_3$ |
| $(CH_2)_3CH_3$ | $(CH_2)_3CH_3$ | H | $(CH_2)_4CH_3$ |
| $(CH_2)_3CH_3$ | $(CH_2)_3CH_3$ | Me | $(CH_2)_4CH_3$ |
| $(CH_2)_3CH_3$ | $(CH_2)_3CH_3$ | H | $(CH_2)_5CH_3$ |
| $(CH_2)_3CH_3$ | $(CH_2)_3CH_3$ | H | $CH_2CH_2CH(CH_3)_2$ |
| $(CH_2)_3CH_3$ | $(CH_2)_3CH_3$ | H | $CH_2CH_2CH(CH_3)_2$ |
| $(CH_2)_3CH_3$ | $(CH_2)_3CH_3$ | H | $CH_2CH(CH_3)CH(CH_3)_2$ |
| $(CH_2)_3CH_3$ | $(CH_2)_3CH_3$ | H | $CH_2(C_5H_9)$ |
| $(CH_2)_3CH_3$ | $(CH_2)_3CH_3$ | H | $CH_2CH_2(C_5H_9)$ |
| $(CH_2)_3CH_3$ | $(CH_2)_3CH_3$ | H | $CH_2(C_6H_{11})$ |
| $(CH_2)_3CH_3$ | $(CH_2)_3CH_3$ | H | $CH_2CH_2(C_6H_{11})$ |
| $(CH_2)_3CH_3$ | $(CH_2)_3CH_3$ | H | $CH_2(C_6H_5)$ |
| $(CH_2)_3CH_3$ | $(CH_2)_3CH_3$ | Me | $CH_2(C_6H_5)$ |
| $(CH_2)_3CH_3$ | $(CH_2)_3CH_3$ | H | $CH_2CH_2(C_6H_5)$ |
| $(CH_2)_3CH_3$ | $(CH_2)_3CH_3$ | Me | $CH_2CH_2(C_6H_5)$ |
| $(CH_2)_3CH_3$ | $(CH_2)_3CH_3$ | H | $CH(CH_3)CH_2CH_3$ |
| $(CH_2)_3CH_3$ | $(CH_2)_3CH_3$ | H | $CH(CH_3)CH_2CH_2CH_3$ |
| $(CH_2)_3CH_3$ | $(CH_2)_3CH_3$ | H | $C(CH_3)_2CH_2CH_3$ |
| $(CH_2)_3CH_3$ | $(CH_2)_3CH_3$ | H | $C(CH_3)_2CH_2CH_2CH_3$ |
| $(CH_2)_3CH_3$ | $(CH_2)_3CH_3$ | H | $CHC(CH_3)_2$ |
| $(CH_2)_3CH_3$ | $(CH_2)_3CH_3$ | H | $CH_2CHC(CH_3)_2$ |
| $(CH_2)_3CH_3$ | $(CH_2)_3CH_3$ | H | $CH_2CH_2OCH_3$ |
| $(CH_2)_3CH_3$ | $(CH_2)_3CH_3$ | H | $CH_2CH_2O(C_6H_5)$ |
| $(CH_2)_3CH_3$ | $(CH_2)_3CH_3$ | H | $CH_2CH_2OCH_2CH_3$ |
| $(CH_2)_3CH_3$ | $(CH_2)_3CH_3$ | H | $CH_2CH_2OCH(CH_3)_2$ |
| $(CH_2)_3CH_3$ | $(CH_2)_3CH_3$ | H | $CH_2OCH_2CH_3$ |
| $(CH_2)_3CH_3$ | $(CH_2)_3CH_3$ | H | $CH_2OCH_2(C_6H_5)$ |
| $(CH_2)_3CH_3$ | $(CH_2)_3CH_3$ | H | $CH_2OCH(CH_3)_2$ |
| $(CH_2)_3CH_3$ | $(CH_2)_3CH_3$ | H | $CH_2OCH_2CH_2CH_3$ |
| $(CH_2)_3CH_3$ | $(CH_2)_3CH_3$ | H | $CH_2OCH_2CH(CH_3)_2$ |
| $(CH_2)_3CH_3$ | $(CH_2)_3CH_3$ | H | $CH_2O(C_6H_5)$ |
| $(CH_2)_3CH_3$ | $(CH_2)_3CH_3$ | H | $CH_2O(C_5H_9)$ |
| $(CH_2)_3CH_3$ | $(CH_2)_3CH_3$ | H | $CH_2OCH_2CH_2OCH_3$ |
| $(CH_2)_3CH_3$ | $(CH_2)_3CH_3$ | H | $CH_2CH_2$-furan-2-yl |
| $(CH_2)_3CH_3$ | $(CH_2)_3CH_3$ | H | $CH_2CH_2$-furan-3-yl |
| $(CH_2)_3CH_3$ | $(CH_2)_3CH_3$ | H | $CH_2CH_2$-thiophene-2-yl |
| $(CH_2)_3CH_3$ | $(CH_2)_3CH_3$ | H | $CH_2CH_2$-thiophene-3-yl |

TABLE C-continued

| R⁶ | R²³ | R⁴ | R²³ᵃ |
|---|---|---|---|
| (CH₂)₃CH₃ | (CH₂)₃CH₃ | H | cyclopropane |
| (CH₂)₃CH₃ | (CH₂)₃CH₃ | H | 2,2-dimethylcyclopropane-1-yl |
| (CH₂)₃CH₃ | (CH₂)₃CH₃ | H | C₅H₉ |
| (CH₂)₃CH₃ | (CH₂)₃CH₃ | H | C₆H₁₁ |
| (CH₂)₃CH₃ | (CH₂)₃CH₃ | H | C₆H₅ |
| (CH₂)₃CH₃ | (CH₂)₃CH₃ | H | 2-CH₃—C₆H₄ |
| (CH₂)₃CH₃ | (CH₂)₃CH₃ | H | 2-CH₃—C₆H₄ |
| (CH₂)₃CH₃ | (CH₂)₃CH₃ | H | 2-CF₃—C₆H₄ |
| (CH₂)₃CH₃ | (CH₂)₃CH₃ | H | 3-CH₃—C₆H₄ |
| (CH₂)₃CH₃ | (CH₂)₃CH₃ | H | 3-CH₂CH₂CH₃—C₆H₄ |
| (CH₂)₃CH₃ | (CH₂)₃CH₃ | H | 3-CF₃—C₆H₄ |
| (CH₂)₃CH₃ | (CH₂)₃CH₃ | H | 3,5-dimethylphenyl-1-yl |
| (CH₂)₃CH₃ | (CH₂)₃CH₃ | H | 3,5 bis(trifluoromethyl)phenyl-1-yl |
| (CH₂)₃CH₃ | (CH₂)₃CH₃ | H | furan-2-yl |
| (CH₂)₃CH₃ | (CH₂₃CH₃ | H | furan-3-yl |
| (CH₂)₃CH₃ | (CH₂)₃CH₃ | H | thiophene-2-yl |
| (CH₂)₃CH₃ | (CH₂)₃CH₃ | H | thiophene-3-yl |
| (CH₂)₃CH₃ | (CH₂)₃CH₃ | H | 3-methylthiophene-2-yl |
| (CH₂)₃CH₃ | (CH₂)₃CH₃ | H | 3-chlorothiophene-2-yl |
| (CH₂)₃CH₃ | (CH₂)₃CH₃ | H | 3-bromothiophene-2-yl |
| (CH₂)₃CH₃ | (CH₂)₃CH₃ | H | 3-methylfuran-2-yl |
| (CH₂)₃CH₃ | (CH₂)₃CH₃ | H | 3-chlorofuran-2-yl |
| (CH₂)₃CH₃ | (CH₂)₃CH₃ | H | 3-bromofuran-2-yl |
| (CH₂)₃CH₃ | (CH₂)₃CH₃ | H | 4-propylphenyl |
| (CH₂)₂CH₃ | (CH₂)₂CH₃ | H | (CH₂)₂CH₃ |
| (CH₂)₂CH₃ | (CH₂)₂CH₃ | H | Butyl |
| (CH₂)₂CH₃ | (CH₂)₂CH₃ | Me | Butyl |
| (CH₂)₂CH₃ | (CH₂)₂CH₃ | H | ⁿPentyl |
| (CH₂)₂CH₃ | (CH₂)₂CH₃ | H | ⁿHexyl |
| (CH₂)₂CH₃ | (CH₂)₂CH₃ | H | CH₂CH(CH₃)₂ |
| (CH₂)₂CH₃ | (CH₂)₂CH₃ | H | CH₂CH₂CH(CH₃)₂ |
| (CH₂)₂CH₃ | (CH₂)₂CH₃ | H | CH₂CH(CH₃)CH(CH₃)₂ |
| (CH₂)₂CH₃ | (CH₂)₂CH₃ | H | CH₂(C₅H₉) |
| (CH₂)₂CH₃ | (CH₂)₂CH₃ | H | CH₂CH₂(C₅H₉) |
| (CH₂)₂CH₃ | (CH₂)₂CH₃ | Me | CH₂CH₂(C₅H₉) |
| (CH₂)₂CH₃ | (CH₂)₂CH₃ | H | CH₂(C₆H₁₁) |
| (CH₂)₂CH₃ | (CH₂)₂CH₃ | H | CH₂CH₂(C₆H₁₁) |
| (CH₂)₂CH₃ | (CH₂)₂CH₃ | H | CH₂(C₆H₅) |
| (CH₂)₂CH₃ | (CH₂)₂CH₃ | H | CH₂CH₂(C₆H₅) |
| (CH₂)₂CH₃ | (CH₂)₂CH₃ | H | CH(CH₃)CH₂CH₃ |
| (CH₂)₂CH₃ | (CH₂)₂CH₃ | H | CH(CH₃)CH₂CH₂CH₃ |
| (CH₂)₂CH₃ | (CH₂)₂CH₃ | H | C(CH₃)₂CH₂CH₃ |
| (CH₂)₂CH₃ | (CH₂)₂CH₃ | H | C(CH₃)₂CH₂CH₂CH₃ |
| (CH₂)₂CH₃ | (CH₂)₂CH₃ | H | CHC(CH₃)₂ |
| (CH₂)₂CH₃ | (CH₂)₂CH₃ | H | CH₂CHC(CH₃)₂ |
| (CH₂)₂CH₃ | (CH₂)₂CH₃ | H | CH₂CH₂OCH₃ |
| (CH₂)₂CH₃ | (CH₂)₂CH₃ | H | CH₂CH₂O(C₆H₅) |
| (CH₂)₂CH₃ | (CH₂)₂CH₃ | H | CH₂CH₂OCH₂CH₃ |
| (CH₂)₂CH₃ | (CH₂)₂CH₃ | H | CH₂CH₂OCH(CH₃)₂ |
| (CH₂)₂CH₃ | (CH₂)₂CH₃ | H | CH₂OCH₂CH₃ |
| (CH₂)₂CH₃ | (CH₂)₂CH₃ | H | CH₂OCH₂(C₆H₅) |
| (CH₂)₂CH₃ | (CH₂)₂CH₃ | H | CH₂OCH(CH₃)₂ |
| (CH₂)₂CH₃ | (CH₂)₂CH₃ | H | CH₂OCH₂CH₂CH₃ |
| (CH₂)₂CH₃ | (CH₂)₂CH₃ | H | CH₂OCH₂CH(CH₃)₂ |
| (CH₂)₂CH₃ | (CH₂)₂CH₃ | H | CH₂O(C₆H₅) |
| (CH₂)₂CH₃ | (CH₂)₂CH₃ | H | CH₂O(C₅H₉) |
| (CH₂)₂CH₃ | (CH₂)₂CH₃ | H | CH₂OCH₂CH₂OCH₃ |
| (CH₂)₂CH₃ | (CH₂)₂CH₃ | H | CH₂CH₂-furan-2-yl |
| (CH₂)₂CH₃ | (CH₂)₂CH₃ | H | CH₂CH₂-furan-3-yl |
| (CH₂)₂CH₃ | (CH₂)₂CH₃ | H | CH₂CH₂-thiophene-2-yl |
| (CH₂)₂CH₃ | (CH₂)₂CH₃ | H | CH₂CH₂-thiophene-3-yl |
| (CH₂)₂CH₃ | (CH₂)₂CH₃ | H | cyclopropane |
| (CH₂)₂CH₃ | (CH₂)₂CH₃ | H | 2,2-dimethylcyclopropane-1-yl |
| (CH₂)₂CH₃ | (CH₂)₂CH₃ | H | C₅H₉ |
| (CH₂)₂CH₃ | (CH₂)₂CH₃ | H | C₆H₁₁ |
| (CH₂)₂CH₃ | (CH₂)₂CH₃ | H | C₆H₅ |
| (CH₂)₂CH₃ | (CH₂)₂CH₃ | H | 2-CH₃—C₆H₄ |
| (CH₂)₂CH₃ | (CH₂)₂CH₃ | H | 2-CH₃—C₆H₄ |
| (CH₂)₂CH₃ | (CH₂)₂CH₃ | H | 2-CF₃—C₆H₄ |
| (CH₂)₂CH₃ | (CH₂)₂CH₃ | H | 3-CH₃—C₆H₄ |
| (CH₂)₂CH₃ | (CH₂)₂CH₃ | H | 3-CH₂CH₂CH₃—C₆H₄ |
| (CH₂)₂CH₃ | (CH₂)₂CH₃ | H | 3-CF₃—C₆H₄ |
| (CH₂)₂CH₃ | (CH₂)₂CH₃ | H | 3-CF₃-5-CF₃—C₆H₃ |
| (CH₂)₂CH₃ | (CH₂)₂CH₃ | H | furan-2-yl |
| (CH₂)₂CH₃ | (CH₂)₂CH₃ | H | furan-3-yl |
| (CH₂)₂CH₃ | (CH₂)₂CH₃ | H | thiophene-2-yl |
| (CH₂)₂CH₃ | (CH₂)₂CH₃ | H | thiophene-3-yl |
| (CH₂)₂CH₃ | (CH₂)₂CH₃ | H | 3-methylthiophene-2-yl |

TABLE C-continued

| R⁶ | R²³ | R⁴ | R²³ᵃ |
|---|---|---|---|
| $(CH_2)_2CH_3$ | $(CH_2)_2CH_3$ | H | 3-chlorothiophene-2-yl |
| $(CH_2)_2CH_3$ | $(CH_2)_2CH_3$ | H | 3-bromothiophene-2-yl |
| $(CH_2)_2CH_3$ | $(CH_2)_2CH_3$ | H | 3-methylfuran-2-yl |
| $(CH_2)_2CH_3$ | $(CH_2)_2CH_3$ | H | 3-chlorofuran-2-yl |
| $(CH_2)_2CH_3$ | $(CH_2)_2CH_3$ | H | 3-bromofuran-2-yl |
| $(CH_2)_2CH_3$ | $(CH_2)_2CH_3$ | H | 4-propylphenyl. |

6. The compound of claim 2 of structural formula:

wherein $C_5H_9$ and $C_6H_{11}$ represent cyclopentyl and cyclohexyl, respectively:

TABLE D

| R⁶ | R²³ | R⁴ᵃ | NR⁴R²³ᵃ |
|---|---|---|---|
| $(CH_2)_3CH_3$ | $(CH_2)_3CH_3$ | H | $NH(CH_2)_2CH_3$ |
| $(CH_2)_3CH_3$ | $(CH_2)_3CH_3$ | H | $NH(CH_2)_3CH_3$ |
| $(CH_2)_3CH_3$ | $(CH_2)_3CH_3$ | H | $NH(CH_2)_4CH_3$ |
| $(CH_2)_3CH_3$ | $(CH_2)_3CH_3$ | H | $NHCH_2CH(CH_3)_2$ |
| $(CH_2)_3CH_3$ | $(CH_2)_3CH_3$ | H | $NH(CH_2)_2CH(CH_3)_2$ |
| $(CH_2)_3CH_3$ | $(CH_2)_3CH_3$ | H | $NHC_5H_9$ |
| $(CH_2)_3CH_3$ | $(CH_2)_3CH_3$ | H | $NHC_6H_{11}$ |
| $(CH_2)_3CH_3$ | $(CH_2)_3CH_3$ | H | $NHC_6H_5$ |
| $(CH_2)_3CH_3$ | $(CH_2)_3CH_3$ | H | NH(3,5-dimethylphen-1-yl) |
| $(CH_2)_3CH_3$ | $(CH_2)_3CH_3$ | H | $NHCH_2(C_6H_5)$ |
| $(CH_2)_3CH_3$ | $(CH_2)_3CH_3$ | H | $NHCH_2$-thiophene-2-yl |
| $(CH_2)_3CH_3$ | $(CH_2)_3CH_3$ | H | $NHCH_2$-thiophene-3-yl |
| $(CH_2)_3CH_3$ | $(CH_2)_3CH_3$ | H | $NH(CH_2)_2OCH_3$ |
| $(CH_2)_3CH_3$ | $(CH_2)_3CH_3$ | H | $NH(CH_2)_2OCH(CH_3)_2$ |
| $(CH_2)_3CH_3$ | $(CH_2)_3CH_3$ | H | morpholine-1-yl |
| $(CH_2)_3CH_3$ | $(CH_2)_3CH_3$ | H | $N(CH_3)(CH_2)_3CH_3$ |
| $(CH_2)_3CH_3$ | $(CH_2)_3CH_3$ | H | $N(CH_3)C_6H_5$ |
| $(CH_2)_3CH_3$ | $(CH_2)_3CH_3$ | H | $N(CH_3)CH_2(C_6H_5)$ |
| $(CH_2)_2CH_3$ | $(CH_2)_2CH_3$ | H | $NH(CH_2)_2CH_3$ |
| $(CH_2)_2CH_3$ | $(CH_2)_2CH_3$ | H | $NH(CH_2)_3CH_3$ |
| $(CH_2)_2CH_3$ | $(CH_2)_2CH_3$ | H | $NH(CH_2)_4CH_3$ |
| $(CH_2)_2CH_3$ | $(CH_2)_2CH_3$ | H | $NHCH_2CH(CH_3)_2$ |
| $(CH_2)_2CH_3$ | $(CH_2)_2CH_3$ | H | $NH(CH_2)_2CH(CH_3)_2$ |
| $(CH_2)_2CH_3$ | $(CH_2)_2CH_3$ | H | $NHC_5H_9$ |
| $(CH_2)_2CH_3$ | $(CH_2)_2CH_3$ | H | $NHC_6H_{11}$ |
| $(CH_2)_2CH_3$ | $(CH_2)_2CH_3$ | H | $NHC_6H_5$ |
| $(CH_2)_2CH_3$ | $(CH_2)_2CH_3$ | H | NH(3,5-dimethylphen-1-yl) |
| $(CH_2)_2CH_3$ | $(CH_2)_2CH_3$ | H | $NHCH_2(C_6H_5)$ |
| $(CH_2)_2CH_3$ | $(CH_2)_2CH_3$ | H | $NHCH_2$-thiophene-2-yl |
| $(CH_2)_2CH_3$ | $(CH_2)_2CH_3$ | H | $NHCH_2$-thiophene-3-yl |
| $(CH_2)_2CH_3$ | $(CH_2)_2CH_3$ | H | $NH(CH_2)_2OCH_3$ |
| $(CH_2)_2CH_3$ | $(CH_2)_2CH_3$ | H | $NH(CH_2)_2OCH(CH_3)_2$ |
| $(CH_2)_2CH_3$ | $(CH_2)_2CH_3$ | H | morpholine-1-yl |
| $(CH_2)_2CH_3$ | $(CH_2)_2CH_3$ | H | $N(CH_3)(CH_2)_2CH_3$ |
| $(CH_2)_2CH_3$ | $(CH_2)_2CH_3$ | H | $N(CH_3)C_6H_5$ |
| $(CH_2)_2CH_3$ | $(CH_2)_2CH_3$ | H | $N(CH_3)CH_2(C_6H_5)$. | wherein:

R⁷ᵃ and R⁷ᵇ are independently: H or CH₃, and all other substitutents are as defined in Table D below, 7. The compound of claim 2 of structural formula:

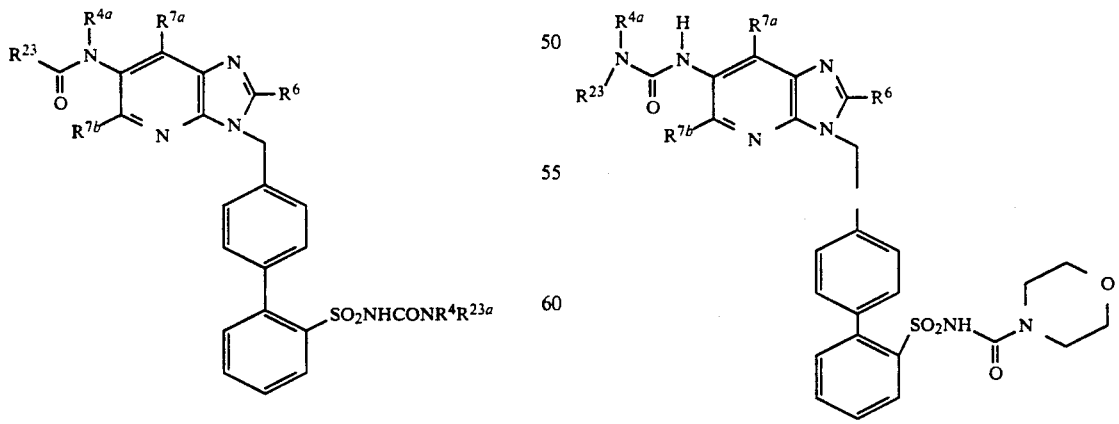

wherein the substituents are as define in Table E below:

TABLE E

| R⁶ | NR⁴ᵃR²³ | R⁷ᵃ | R⁷ᵇ |
|---|---|---|---|
| (CH₂)₃CH₃ | NHEt | H | H |
| (CH₂)₃CH₃ | NHEt | H | CH₃ |
| (CH₂)₃CH₃ | NHEt | CH₃ | H |
| (CH₂)₃CH₃ | NHEt | CH₃ | CH₃ |
| (CH₂)₂CH₃ | NHEt | H | H |
| (CH₂)₂CH₃ | NHEt | H | CH₃ |
| (CH₂)₂CH₃ | NHEt | CH₃ | H |
| (CH₂)₂CH₃ | NHEt | CH₃ | CH₃ |
| (CH₂)₃CH₃ | NHPr | H | H |
| (CH₂)₃CH₃ | NHPr | H | CH₃ |
| (CH₂)₃CH₃ | NHPr | CH₃ | H |
| (CH₂)₃CH₃ | NHPr | CH₃ | CH₃ |
| (CH₂)₂CH₃ | NHPr | H | H |
| (CH₂)₂CH₃ | NHPr | H | CH₃ |
| (CH₂)₂CH₃ | NHPr | CH₃ | H |
| (CH₂)₂CH₃ | NHPr | CH₃ | CH₃ |
| (CH₂)₃CH₃ | NH-iso Pr | H | H |
| (CH₂)₃CH₃ | NH-iso Pr | H | CH₃ |
| (CH₂)₃CH₃ | NH-iso-Pr | CH₃ | H |
| (CH₂)₃CH₃ | NH-iso-Pr | CH₃ | CH₃ |
| (CH₂)₂CH₃ | NH-iso-Pr | H | H |
| (CH₂)₂CH₃ | NH-iso-Pr | H | CH₃ |
| (CH₂)₂CH₃ | NH-iso-Pr | CH₃ | H |
| (CH₂)₂CH₃ | NH-iso-Pr | CH₃ | CH₃ |
| (CH₂)₂CH₃ | N(CH₃)-iso-Pr | H | H |
| (CH₂)₃CH₃ | N(CH₃)-iso-Pr | H | CH₃ |
| (CH₂)₃CH₃ | N(CH₃)-iso-Pr | CH₃ | H |
| (CH₂)₃CH₃ | N(CH₃)-iso-Pr | CH₃ | CH₃ |
| (CH₂)₂CH₃ | N(CH₃)-iso-Pr | H | H |
| (CH₂)₂CH₃ | N(CH₃)-iso-Pr | H | CH₃ |
| (CH₂)₂CH₃ | N(CH₃)-iso-Pr | CH₃ | H |
| (CH₂)₂CH₃ | N(CH₃)-iso-Pr | CH₃ | CH₃ |

8. The compound of claim 2 of structural formula:

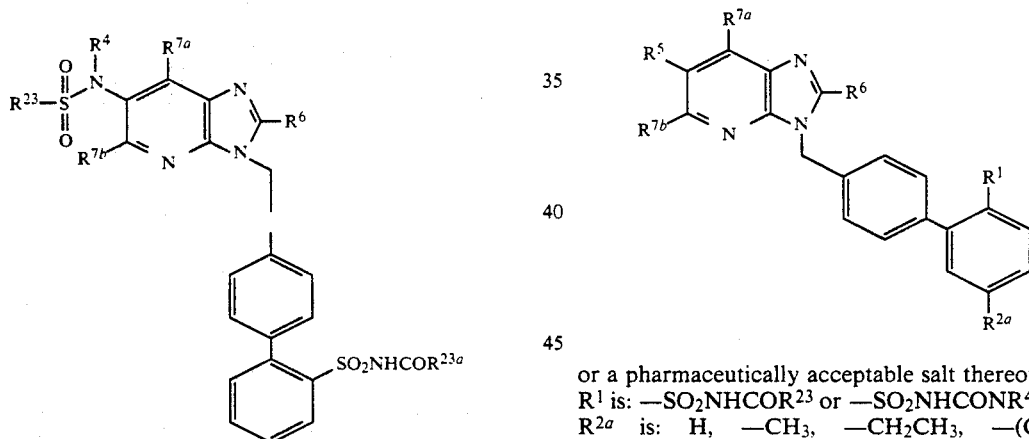

wherein:
$R^{7a}$ and $R^{7b}$ are independently: H or CH₃, and all other substitutents are as defined in Table F below:

or a pharmaceutically acceptable salt thereof, wherein:
$R^1$ is: —SO₂NHCOR²³ or —SO₂NHCONR⁴R²³;
$R^{2a}$ is: H, —CH₃, —CH₂CH₃, —(CH₂)₂CH₃, —CH(CH₃)₂, —CH₂CH(CH₃)₂, —OCH₂CH₃, or —OCH₂CF₃;
$R^5$ is:
—N(R⁴)COR²³,
—NHSO₂R²³,
—N(R⁴)CO₂R²³,
—N(R⁴)CON(R⁴)R²³, or

TABLE F

| R⁶ | R²³ | R⁴ | R²³ᵃ |
|---|---|---|---|
| (CH₂)₃CH₃ | Bu | H | (CH₂)₃CH₃ |
| (CH₂)₃CH₃ | Bu | H | CH₂CH₂C₆H₅ |
| (CH₂)₃CH₃ | Bu | Me | (CH₂)₃CH₃ |
| (CH₂)₃CH₃ | Bu | H | CH₂CH₂C₆H₅ |
| (CH₂)₃CH₃ | Bu | H | CH₂CH₂CH(CH₃)₂ |
| (CH₂)₂CH₃ | Bu | H | (CH₂)₃CH₃ |
| (CH₂)₂CH₃ | Bu | H | CH₂CH₂C₆H₅ |
| (CH₂)₂CH₃ | Bu | Me | (CH₂)₃CH₃ |
| (CH₂)₂CH₃ | Bu | H | CH₂CH₂C₆H₅ |
| (CH₂)₂CH₃ | Bu | H | CH₂CH₂CH(CH₃)₂ |

9. The compound of claim 2 of structural formula III

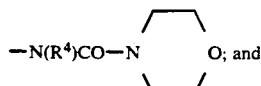

R⁶ is: ethyl, propyl, butyl, cyclopropyl, ethyloxy or propyloxy.

10. The compound of claim 9 of structural formula

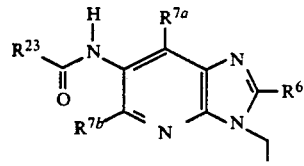

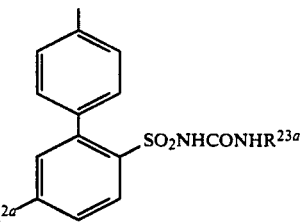

wherein:
R⁷ᵃ and R⁷ᵇ are independently: H or CH₃, and all other substitutents are as defined in Table H below:

TABLE H

| R⁶ | R²³ | R²³ᵃ | R²ᵃ |
|---|---|---|---|
| (CH₂)₃CH₃ | (CH₂)₃CH₃ | (CH₂)₃CH₃ | Pr |
| (CH₂)₂CH₃ | (CH₂)₂CH₃ | (CH₂)₃CH₃ | Pr |
| (CH₂)₃CH₃ | (CH₂)₃CH₃ | (CH₂)₃CH₃ | Et |
| (CH₂)₂CH₃ | (CH₂)₂CH₃ | (CH₂)₃CH₃ | Et |
| (CH₂)₂CH₃ | (CH₂)₂CH₃ | (CH₂)₃CH₃ | iso-Bu. |

12. The compound of claim 9 of structural formula

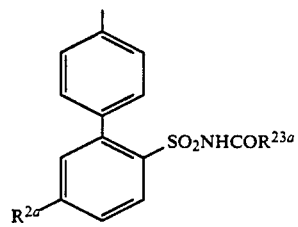

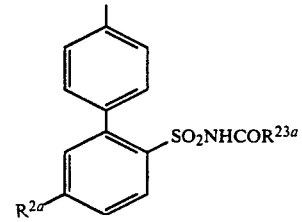

wherein:
R⁷ᵃ and R⁷ᵇ are independently: H or CH₃, and all other substitutents are as defined in Table G below, wherein C₅H₉ represents cyclopentyl:

TABLE G

| R⁶ | R²³ | R²³ᵃ | R²ᵃ |
|---|---|---|---|
| (CH₂)₃CH₃ | (CH₂)₃CH₃ | (CH₂)₃CH₃ | Pr |
| (CH₂)₃CH₃ | (CH₂)₃CH₃ | CH₂CH₂(C₅H₉) | Pr |
| (CH₂)₃CH₃ | (CH₂)₃CH₃ | CH₂CH₂OCH₂CH₃ | Pr |
| (CH₂)₃CH₃ | (CH₂)₃CH₃ | C₆H₅ | Pr |
| (CH₂)₃CH₃ | (CH₂)₃CH₃ | (CH₂)₃CH₃ | Et |
| (CH₂)₃CH₃ | (CH₂)₃CH₃ | CH₂CH₂(C₅H₉) | Et |
| (CH₂)₃CH₃ | (CH₂)₃CH₃ | CH₂CH₂OCH₂CH₃ | Et |
| (CH₂)₃CH₃ | (CH₂)₃CH₃ | C₆H₅ | Et |
| (CH₂)₂CH₃ | (CH₂)₂CH₃ | CH₂CH₂(C₆H₅) | Pr |
| (CH₂)₂CH₃ | (CH₂)₂CH₃ | CH₂CH₂(C₆H₅) | Et |
| (CH₂)₂CH₃ | (CH₂)₂CH₃ | (CH₂)₃CH₃ | Pr |
| (CH₂)₂CH₃ | (CH₂)₂CH₃ | (CH₂)₃CH₃ | Et |
| (CH₂)₂CH₃ | (CH₂)₂CH₃ | C₆H₅ | Pr |
| (CH₂)₂CH₃ | (CH₂)₂CH₃ | C₆H₅ | Et |
| (CH₂)₃CH₃ | (CH₂)₃CH₃ | CH₂CH₂OCH₂CH₃ | iso-Bu |
| (CH₂)₃CH₃ | (CH₂)₃CH₃ | (CH₂)₃CH₃ | iso-Bu. |

11. The compound of claim 9 of structural formula

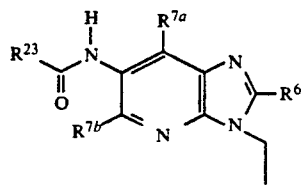

wherein:
R⁷ᵃ and R⁷ᵇ are independently: H or CH₃, and all other substitutents are as defined Table I below, wherein C₅H₉ represents cyclopentyl:

TABLE I

| R⁶ | R²³ | R²³ᵃ | R²ᵃ |
| --- | --- | --- | --- |
| CH₂CH₃ | Et | (CH₂)₃CH₃ | Pr |
| CH₂CH₃ | CH₃ | CH₂CH₂C₅H₉) | Pr |
| (CH₂)₃CH₃ | iso-Pr | (CH₂)₃CH₃ | Pr |
| CH₂CH₃ | iso-Pr | CH₂CH₂(C₅H₉) | Pr |
| (CH₂)₂CH₃ | iso-Pr | (CH₂)₃CH₃ | Pr |
| CH₂CH₃ | Et | (CH₂)₃CH₃ | Et |
| CH₂CH₃ | CH₃ | CH₂CH₂(C₅H₉) | Et |
| (CH₂)₃CH₃ | iso-Pr | (CH₂)₃CH₃ | Et |
| CH₂CH₃ | iso-Pr | CH₂CH₂(C₅H₉) | Et |
| (CH₂)₂CH₃ | iso-Pr | (CH₂)₃CH₃ | Et |
| CH₂CH₃ | Et | (CH₂)₃CH₃ | iso-Bu |
| CH₂CH₃ | CH₃ | CH₂CH₂(C₅H₉) | iso-Bu |
| (CH₂)₃CH₃ | iso-Pr | (CH₂)₃CH₃ | iso-Bu |
| CH₂CH₃ | iso-Pr | CH₂CH₂(C₅H₉) | iso-Bu |
| (CH₂)₂CH₃ | iso-Pr | (CH₂)₃CH₃ | iso-Bu. |

13. The compound of claim 9 of structural formula R⁷ᵃ and R⁷ᵇ are independently: H or CH₃, and all other substitutents are as defined in Table J below:

TABLE J

| R⁶ | R²³ | R²³ᵃ | R²ᵃ |
| --- | --- | --- | --- |
| (CH₂)₂CH₃ | Et | (CH₂)₃CH₃ | Pr |
| (CH₂)₂CH₃ | Et | (CH₂)₃CH₃ | Pr |
| CH₂CH₃ | Et | (CH₂)₃CH₃ | Pr |
| CH₂CH₃ | CH₃ | (CH₂)₃CH₃ | Pr |
| (CH₂)₃CH₃ | iso-Pr | (CH₂)₃CH₃ | Pr |
| CH₂CH₃ | iso-Pr | (CH₂)₃CH₃ | Pr |
| (CH₂)₂CH₃ | iso-Pr | (CH₂)₃CH₃ | Pr |
| (CH₂)₂CH₃ | Et | (CH₂)₃CH₃ | Et |
| (CH₂)₃CH₃ | Et | (CH₂)₃CH₃ | Et |
| CH₂CH₃ | Et | (CH₂)₃CH₃ | Et |
| CH₂CH₃ | CH₃ | (CH₂)₃CH₃ | Et |
| (CH₂)₃CH₃ | iso-Pr | (CH₂)₃CH₃ | Et |
| CH₂CH₃ | iso-Pr | (CH₂)₃CH₃ | Et |
| (CH₂)₂CH₃ | iso-Pr | (CH₂)₃CH₃ | Et |
| (CH₂)₂CH₃ | Et | (CH₂)₃CH₃ | iso-Bu |
| (CH₂)₃CH₃ | Et | (CH₂)₃CH₃ | iso-Bu |
| CH₂CH₃ | Et | (CH₂)₃CH₃ | iso-Bu |
| CH₂CH₃ | CH₃ | (CH₂)₃CH₃ | iso-Bu |
| (CH₂)₃CH₃ | iso-Pr | (CH₂)₃CH₃ | iso-Bu |
| CH₂CH₃ | iso-Pr | (CH₂)₃CH₃ | iso-Bu |
| (CH₂)₂CH₃ | iso-Pr | (CH₂)₃CH₃ | iso-Bu. |

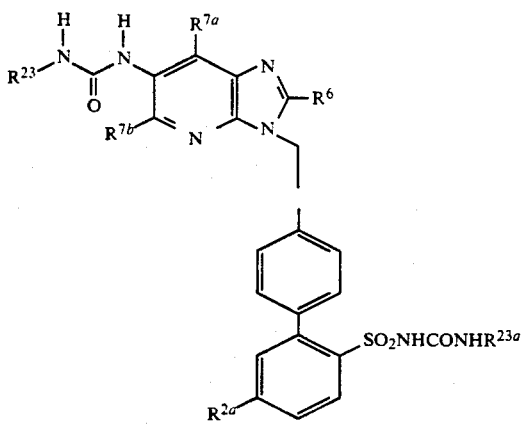

wherein:

14. A pharmaceutical composition useful in the treatment of hypertension which comprises a pharmaceutically acceptable carrier and a therapeutically effective amount of a compound of claim 1.

15. A method of treating hypertension which comprises administering to a patient in need of such treatment a therapeutically effective amount of a compound of claim 1.

16. An ophthalmological formulation for the treatment of ocular hypertension comprising an ophthalmologically acceptable carrier and an effective ocular antihypertensive amount of a compound of claim 1.

17. A method of treating ocular hypertension comprising topical ocular administration to a patient in need of such treatment of an effective ocular antihypertensive amount of a compound of claim 1.

18. A method of treating cognitive dysfunction, anxiety, or depression comprising administering to a patient in need of such treatment, a therapeutically effective amount of a compound of claim 1.

* * * * *